US010758591B2

(12) United States Patent
Frisbee et al.

(10) Patent No.: US 10,758,591 B2
(45) Date of Patent: Sep. 1, 2020

(54) COMPOSITIONS AND METHODS FOR TREATING CLOSTRIDIUM DIFFICILE INFECTION

(71) Applicant: University of Virginia Patent Foundation, Charlottesville, VA (US)

(72) Inventors: Alyse Longtin Frisbee, Charlottesville, VA (US); William A. Petri, Jr., Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/317,887

(22) PCT Filed: Jul. 25, 2017

(86) PCT No.: PCT/US2017/043651
§ 371 (c)(1),
(2) Date: Jan. 15, 2019

(87) PCT Pub. No.: WO2018/022575
PCT Pub. Date: Feb. 1, 2018

(65) Prior Publication Data
US 2019/0290732 A1  Sep. 26, 2019

Related U.S. Application Data

(60) Provisional application No. 62/366,761, filed on Jul. 26, 2016, provisional application No. 62/366,750, filed on Jul. 26, 2016.

(51) Int. Cl.
| | |
|---|---|
| *A61K 38/14* | (2006.01) |
| *C07K 14/54* | (2006.01) |
| *A61K 45/06* | (2006.01) |
| *A61K 38/20* | (2006.01) |
| *A61P 31/04* | (2006.01) |
| *A61K 31/4164* | (2006.01) |
| *A61K 39/395* | (2006.01) |
| *A61P 1/04* | (2006.01) |
| *A61K 31/7036* | (2006.01) |
| *A61K 31/426* | (2006.01) |
| *A61K 38/00* | (2006.01) |
| *A61K 31/437* | (2006.01) |
| *A61K 31/7042* | (2006.01) |
| *A61K 31/7048* | (2006.01) |

(52) U.S. Cl.
CPC .......... *A61K 38/20* (2013.01); *A61K 31/4164* (2013.01); *A61K 31/426* (2013.01); *A61K 31/437* (2013.01); *A61K 31/7036* (2013.01); *A61K 31/7042* (2013.01); *A61K 31/7048* (2013.01); *A61K 38/00* (2013.01); *A61K 38/14* (2013.01); *A61K 39/39541* (2013.01); *A61K 45/06* (2013.01); *A61P 1/04* (2018.01); *A61P 31/04* (2018.01); *C07K 14/54* (2013.01)

(58) Field of Classification Search
None
See application file for complete search history.

(56) References Cited

U.S. PATENT DOCUMENTS

| | | | |
|---|---|---|---|
| 10,046,030 | B2 | 8/2018 | Petri, Jr. et al. |
| 10,196,453 | B2 | 2/2019 | Cowardin et al. |
| 2015/0259645 | A1 | 9/2015 | Inserm et al. |
| 2015/0306139 | A1 | 10/2015 | Ravetch et al. |

FOREIGN PATENT DOCUMENTS

| | | |
|---|---|---|
| WO | WO 2015/042521 | 3/2015 |
| WO | WO 2016/057671 A1 | 4/2016 |

OTHER PUBLICATIONS

Akira, S. & Takeda, K. Toll-like receptor signalling. Nat. Rev. Immunol. 4, pp. 499-511 (2004).
Andrews et al., "TLR2 Regulates Neutrophil Recruitment and Cytokine Production with Minor Contributions from TLR9 during Hypersensitivity Pneumonitis," PLoS One, vol. 8, (2013).
Aslam et al., Treatment of Clostridium difficile-associated disease: old therapies and new strategies. Lancet Infect. Dis. 5, 549-57 (2005).
Bartlett, "Annals of Internal Medicine Review Narrative Review: The New Epidemic of Clostridium difficile," An. Intern. Med. pp. 758-764 (2006).
Buonomo et al., "Microbiota-Regulated IL-25 Increases Eosinophil Number to Provide Protection during Clostridium difficile Infection," Cell Rep. pp. 432-443 (2016).

(Continued)

*Primary Examiner* — Padmavathi Baskar
(74) *Attorney, Agent, or Firm* — Jenkins, Wilson, Taylor & Hunt, P.A.

(57) ABSTRACT

*Clostridium difficile* infection is the leading cause of hospital acquired antibiotic-associated diarrhea in the US (Bartlett, in 2006). The increased prevalence of circulating *C. difficile* strains poses a significant health threat to US health care facilities. Strains expressing the toxin *C. difficile* Transferase (CDT), in addition to Toxins A and B (TcdA and TcdB), are more virulent and are associated with higher mortality rates (Bacci et al., 2011). We recently identified a protective role for eosinophils against *C. difficile* pathogenesis (Buonomo et al., 2016). We have also defined CDT's ability to increase host inflammation and suppress protective eosinophils through a TLR2 dependent mechanism (Cowardin et al., 2016). How CDT promotes virulence and eosinophil suppression via TLR2 is still under investigation. We employed a genome-wide microarray approach to reveal divergent transcriptional profiles between protected (TLR2−/−) and unprotected (WT) mice infected with either CDT expressing or CDT mutant strains of *C. difficile*. This work revealed novel host mediated TLR2-dependent inflammatory pathways to CDT. We provide an unbiased framework for understanding the host immune response to the binary toxin CDT produced by *C. difficile* and how TLR2 signaling enhances virulence.

23 Claims, 20 Drawing Sheets
(15 of 20 Drawing Sheet(s) Filed in Color)
Specification includes a Sequence Listing.

(56) References Cited

OTHER PUBLICATIONS

Buonomo et al., "Role of interleukin 23 signaling in clostridium difficile colitis," Journal of Infectious Diseases, vol. 208 pp. 917-920 (2013).
Cowardin et al., The binary toxin CDT enhances Clostridium difficile virulence by suppressing protective colonic eosinophilia. Nat. Microbiol. 1, 1-10 (2016) (1(8): 16108, doi:10.1038/nmicrobiol.2016.108., Published online: Jul. 11, 2016).
Cowardin et al., "Inflammasome activation contributes to interleukin-23 production in response to Clostridium difficile," MBio vol. 6, pp. 1-9 (2015).
Gerding et al., "Clostridium difficile binary toxin CDT: mechanism, epidemiology, and potential clinical importance," Gut microbes vol. 5, pp. 15-27 (2014).
Haraldsen et al., "Interleukin-33—cytokine of dual function or novel alarmin?" Trends in Immunology, vol. 30 pp. 227-233 (2009).
Infectious National Institute of Allergy and Diseases, NIAID a€TMs Antibacterial Resistance Program: Current Status and Future Directions (2014).
International Preliminary Report on Patentability corresponding to PCT/US2017/043651 dated Jan. 29, 2019.
International Search Report corresponding to PCT/US2017/043651 dated Jan. 8, 2018.
Kuehne et al., "Importance of toxin a, toxin b, and cdt in virulence of an epidemic clostridium difficile strain," J. Infect. Dis. vol. 209 pp. 83-86 (2014).
Schiering et al., "The alarmin IL-33 promotes regulatory T-cell function in the intestine," Nature, vol. 513 pp. 564-568 (2014).
Written Opinion of International Searching Authority corresponding to PCT/US2017/043651 dated Jan. 8, 2018.

COMPOSITIONS AND METHODS FOR TREATING CLOSTRIDIUM DIFFICILE INFECTION

CROSS REFERENCE TO RELATED APPLICATIONS

This application is a national stage filing of International Application No. PCT/US2017/043651, filed Jul. 25, 2017, which claims priority under 35 U.S.C. § 119(e) to U.S. Provisional Application Ser. Nos. 62/366,761 and 62/366,750 filed Jul. 26, 2016, the disclosures of which are incorporated by reference in their entirety herein.

STATEMENT REGARDING FEDERALLY SPONSORED RESEARCH OR DEVELOPMENT

This invention was made with government support under Grant No. AI124214 awarded by The National Institutes of Health. The government has certain rights in the invention.

BACKGROUND

*Clostridium difficile* (*C. difficile*) is a gram-positive, spore-forming anaerobe that infects the gut when the natural flora has been disrupted, primarily through antibiotic treatment. It is currently the leading cause of nosocomial infections in the United States, resulting in approximately 29,000 deaths per year and costing the US health care system an estimated $4.8 billion annually. Disease can range from asymptomatic colonization, to mild diarrhea, to life threatening pseudomembranous colitis and toxic megacolon. A hypervirulent strain of *C. difficile* is the cause of 30-day mortality in up to 15% of patients diagnosed with *C. difficile* infection (CDI). Current therapy involves removal of the offending antibiotic and starting vancomycin or metronidazole treatment, which can inhibit the reestablishment of beneficial endogenous flora while fighting infection. Despite therapy, recurrent disease is seen in 10-35% of patients after their initial case of CDI and in 35-65% of patients after primary reoccurrence, stressing the need for more effective therapies. It has been hypothesized that the degree of disease severity correlates with the intensity of the host response. Therefore, a better understanding of the mechanism by which immune response provides production is important to develop therapies that modulate the host inflammatory response as a novel way to treat disease.

Over the past decade, epidemic, hypervirulent strains of *C. difficile* (NAPI/027 strains) have emerged with higher relapse rates and increased resistance to antibiotics; the current standard of care to treat CDI (6, 8). These epidemic strains have acquired the expression of a third toxin, binary toxin (CDT), in addition to previously expressed Toxins A and B (TcdA and TcdB) (8). CDT is composed of two subunits: CDTb is the binding subunit and CDTa is the enzymatic subunit. To intoxicate host cells, CDTb associates with a host cell surface receptor, thought to be the lipolysis-stimulated lipoprotein receptor (LSR) (9) and the enzymatic CDTa subunit destabilizes of the cellular cytoskeleton through ADP-ribosylation of actin (8). Our lab has discovered that CDT toxin increases the virulence of epidemic NAPI/027 strains of *C. difficile*. Furthermore, we have shown that CDT is sensed by toll-like receptor 2 (TLR2) to mount a detrimental pro-inflammatory immune response (10). Interestingly, our studies showed that CDT mediated activation of the TLR2 pathway is pathogenic for the host during *C. difficile* infection as TLR2−/− mice are significantly protected from NAPI/027 associated mortality (See FIGS. 1-3).

There is a long felt need in the art for compositions and methods useful for preventing and treating *C. difficile* infections. The present invention satisfies this need.

SUMMARY OF THE INVENTION

*C. difficile* colitis is the number one health care-associated infection in North America. It has a 15% mortality despite appropriate antibiotic therapy. There is thus a need for new therapeutic approaches. The invention builds on our previous work teaching that IL-25-induced eosinophilia is protective (see PCT/US2015/054498) and that TLR2 antagonists would be protective against *C. difficile* colitis (Cowardin et al., Nature Microbiology, epublished Jul. 11, 2016, "The binary toxin CDT enhances *C. difficile* virulence by suppressing protective colonic eosinophilia").

It is disclosed herein, based on a genome wide gene expression analysis, that interleukin-33 (IL-33) is a candidate of interest as it was increased in the colons of protected TLR2−/− mice during *C. difficile* infection. Based on these results further studies (see Examples) were performed and demonstrate that IL-33 treatment protects from NAPI/027-associated mortality and weight-loss during *C. difficile* infection by skewing the immune response in the colon and by induction of regulatory T-cells. This work has the potential to inform novel immunotherapies to treat epidemic *C. difficile* infection.

The present application discloses that IL-33 comprises a parallel pathway to IL-25 to induce protection from *C. difficile* and reduce mortality and severity of infection, as well as reduce signs associated with the infection. This pathway can be induced to treat or prevent *C. difficile* not only by stimulation of IL-33 (by microbiota transplants for example), or by small molecule agonists of the IL-33 signaling pathway, but also by TLR2 antagonists (since TLR2 activation potentiates the lethal effects of the *C. difficile* transferase (CDT) toxin of the epidemic strain of *C. difficile*). Therefore, the present invention encompasses the use of compositions and methods to counteract the effects of infection, such as by stimulating IL-33 expression, levels, and activity as well as administering IL-33. It is also disclosed herein that IL-33 treatment protects against R20291 (CDT+) virulence independent of the *C. difficile* burden and it protects against weight loss. It is further disclosed herein that IL-33 treatment increases ST2+ regulatory T-cells during *C. difficile* infection.

It is also disclosed that IL-33 treatment acts as an anti-inflammatory agent. In one aspect, it reduces detrimental colonic inflammation during *C. difficile* infection.

The present invention further encompasses the use of microbiota transplants that stimulate IL-33 or molecules that activate the IL-33 pathway upstream or downstream of the IL-33 receptor.

Hypervirulent strains of *C. difficile* express an additional toxin, *C. difficile* transferase (CDT) that contributes to increased virulence. An Affymetrix microarray was used to identify gene expression changes within infected ceca of CDT+ and CDT− infected mice (see Examples). Also analyzed was CDT mediated gene expression changes in both susceptible wildtype mice and TLR2−/− mice, which we have previously shown to be protected from CDT virulence. Through this array, IL-33 was identified as a gene significantly elevated in protected TLR2−/− mice. To further determine whether IL-33 is protective during *C. difficile* infection, recombinant IL-33 was administered to mice prior to and during *C. difficile* infection, resulting in highly significant protection from mortality and weight-loss.

Various prior disease states and conditions are known to increase susceptibility to *C. difficile* infection. In one embodiment, the present invention provides compositions and methods for prophylactically treating susceptible subjects to reduce the severity of an infection or to prevent infection by pre-treating the subject with a composition of the invention. One of ordinary skill in the art can determine if a subject is susceptible to CDI and can design a treatment regimen accordingly. In one embodiment, the invention provides compositions and methods useful for prevention of a *C. difficile* infection in a subject who becomes susceptible to a *C. difficile* infection. In one embodiment, a subject becomes susceptible to *C. difficile* infection due to prior antibiotic therapy that may lead to *C. difficile* infection. Support for this treatment is disclosed herein (FIG. 11). Mice administered a cocktail of broad-spectrum antibiotics were found to have a significant reduction in IL-33 protein within their colons; supporting the notion that replenishing IL-33 may be an important therapy for preventing severe *C. difficile* infection after antibiotic treatment.

In one aspect, the method comprises administering to a subject an effective amount of IL-33, or a biologically active fragment or homolog thereof. In one aspect, the IL-33 protein comprises an amino acid sequence selected from the group consisting of SEQ ID NOs:1, 2, 3, 4, 5, 6, 7, 8, 9, 10, 11, and 12, and biologically active fragments and homologs thereof. The present invention further encompasses the use of active isoforms of IL-33. A summary of all sequences used herein is provided in the "Embodiments" section below. Fragments can include one or more amino acid residue deletions.

The present invention further provides for the use of IL-33 peptides with conservative amino acid substitutions that do not have a substantial effect on the activity described herein. For example, there can be up to 20 or up to about 10 conservative amino acid substitutions. In one aspect, there are 1, 2, 3, 4, 5, 6, 7, 8, 9, or 10 substitutions.

Useful homologs of IL-33 and its active fragments can have varying homologies as long as the homologous peptide has similar activity. In one aspect, the homology can be at least about 75, 80, 85, 90, 95, and 99% homology with the IL-33 peptide or fragment.

Effective doses of IL-33 can vary depending on the age, sex, weight, and health of the subject and a dosage regimen or strategy can be developed by one of ordinary skill in the art.

In one embodiment, an effective dose of IL-33 or a biologically active fragment or homolog thereof ranges from about 0.1 μg/kg body weight to about 1,000 μg/kg body weight. In one aspect, the dosage is from about 1.0 μg/kg body weight to about 500 μg/kg body weight. In another aspect, the dosage is from about 5.0 μg/kg body weight to about 200 μg/kg body weight. In a further aspect, the dosage is from about 10 μg/kg body weight to about 100 μg/kg body weight. In another aspect, the dosage is selected from the group consisting of 1.0, 2.0, 3.0, 4.0, 5.0, 6.0, 7.0, 8.0, 9.0, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, and 500 μg/kg of body weight.

Clinical doses of proteins or biologically active fragments or homologs thereof are disclosed herein and are also known in the art. Doses can vary depending on the age, sex, weight, body surface area (BSA), and health of the subject, as well as the specific sign(s) of the infection being treated. Additionally, a higher dose may be used in some cases where an immediate effect is needed. Doses can be administered as a unit dose or the dose can be based on criteria such as those described above for body weight, etc. Doses can also be divided if administered more than once per day.

The number of doses of IL-33 to be administered can also vary depending on the age, sex, weight, body surface area (BSA), and health of the subject, as well as the specific sign(s) of the infection being treated. A pharmaceutical composition of the invention can be administered, for example, 1, 2, 3, 4, 5, 6, 7, 8, 9, or 10 times. In one aspect, it can be administered up to 20 times. In one aspect, it is administered once daily. In another aspect it is administered more than once in a day. In one aspect, it is administered once per week. In another aspect, it is administered more than once per week. In one aspect, it is administered once per month. In another aspect, it is administered more than once per month.

The present invention is useful for treating and preventing CDI and *C. difficile* colitis, including reducing mortality, preventing or inhibiting recurrent infection, inhibiting weight loss, inhibiting diarrhea, inhibiting colonic inflammation, and increasing colonic Foxp3+ ST2+ regulatory T cells during the infection. In one aspect, the inflammation is neutrophil inflammation. In another aspect, the inflammation is monocyte inflammation. In one aspect, the inflammation is associated with both neutrophil and monocyte inflammation. In one aspect, the compositions and methods of the invention are useful for replenishing IL-33 that has been depleted by antibiotic therapy.

In one embodiment, the invention encompasses the use of at least one additional therapeutic agent. Based on the teachings herein, one of ordinary skill in the art can determine which therapeutic agent(s) to administer, which can be, for example, an anesthetic, analgesic, antimicrobial, steroid, growth factor, cytokine, anti-inflammatory agent, drugs, probiotics, and pre-biotics. In one aspect, the antimicrobial agent can be, for example, an antibacterial, antifungal, or antiviral agent. In one aspect, an antibiotic useful for the present method includes, but is not limited to, vancomycin, fidaxomicin, metronidazole, nitazoxanide, and rifaximin.

The present invention further provides for combination therapies encompassing IL-33, IL-25, and regulation of TLRs.

It is disclosed herein that IL-33 comprises a parallel pathway to IL-25 for protection against *C. difficile*.

In one embodiment, the present invention encompasses a combination therapy using IL-33 and an effective amount of an inhibitor of Toll-Like Receptor 2 (TLR2). In one aspect, the inhibitor inhibits stimulation of TLR2 activity by *Clostridium difficile* transferase toxin, thereby inhibiting the effects of *Clostridium difficile* transferase toxin. In one aspect, an inhibitor of the invention includes, but is not limited to, an antibody, antibody fragment, humanized antibody, monoclonal antibody, aptamer, phylomer, antisense oligonucleotide, nucleic acid, siRNA, protein, and a drug. In one aspect, a monoclonal antibody of the invention is directed against TLR2. In one aspect, a monoclonal antibody of the invention includes, but is not limited to, clone B4H2, clone C9A12, clone T2.5, clone mAb2616, clone TL2.1, and clone EPNCIR133.

In one embodiment, the compositions and methods of the invention are useful for protecting against CDT mediated virulence.

The present invention further encompasses kits for treating subjects in need thereof. The kits may comprise IL-33 and biological fragments or homologs thereof, antimicrobials, inhibitors of TLR2, an applicator, and an instructional material.

Various aspects and embodiments of the invention are described in further detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4, comprising FIGS. 4A-4C, demonstrates that IL-33 IS UPREGULATED BY CDT TOXIN IN PROTECTED TLR2−/− MICE—Experimental design of Affymetrix microarray to identify gene expression changes in protected TLR2−/− and susceptible wildtype mice infected with CDT+ or CDT− R20291 (FIG. 4A). Protected TLR2−/− mice have fewer genes upregulated in response to CDT toxin in their colon compared to wildtype mice (Fold Change>1.5; adj P<−0.3) (FIG. 4B). IL-33, identified via micro array, is significantly increased in protected TLR2−/− mice compared to wildtype mice during CDT+ or CDT− *C. difficile* infection (FIG. 4C).

FIG. 5, comprising FIGS. 5A and 5B, demonstrates graphically that IL-33 TREATMENT PROTECTS FROM MORTALITY—Mice treated with recombinant IL-33 (5 days prior to infection) are significantly protected from mortality (FIG. 5A) independent of *C. difficile* bacterial burden (FIG. 5B).

FIG. 6, comprising FIGS. 6A-6D, demonstrates graphically that IL-33 TREATMENT REDUCES COLONIC INFLAMMATION DURING CDI. IL-33 treatment reduces colonic neutrophilic (FIG. 6A) and $Ly6C^{hi}$ monocyte inflammation (FIG. 6B) during *C. difficile* infection. Representative flow dot plots of monocyte and neutrophil populations in the colon during *C. difficile* infection in PBS treatment group (FIG. 6C) and IL-33 treatment group (FIG. 6D).

FIG. 7, comprising FIGS. 7A-7D, demonstrates graphically that IL-33 TREATMENT INCREASES ST2+ REGULATORY T CELLS IN THE COLON DURING CDI. IL-33 treatment increases colonic regulatory T-cells (FIG. 7A) and increases ST2 (IL-33R) expression on T-regs (FIG. 7B) during *C. difficile* infection. Representative flow dot plots ST2+ Foxp3+ CD4+ T cells in the colon during CDI in PBS treatment group (FIG. 7C) and IL-33 treatment group (FIG. 7D).

DETAILED DESCRIPTION

Abbreviations and Acronyms

Figure 1:
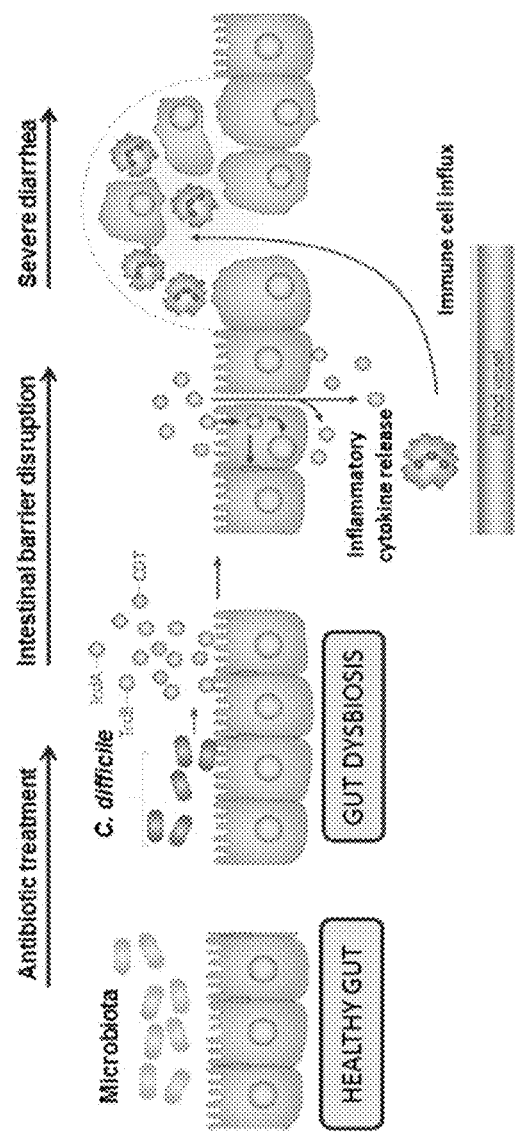
FIG. 1. SCHEMATIC REPRESENTATION OF PATHOGENESIS OF *C. DIFFICILE* INFECTION (CDI) IN THE COLON. In a healthy gut, the microbiota and host epithelial cells maintain normal metabolism and homeostasis; however disruption of the microbiota by antibiotics leads to dysbiosis and altered microbiome. This allows for *C. difficile* to colonize the gut where it releases toxin A and B.
Figure 2:
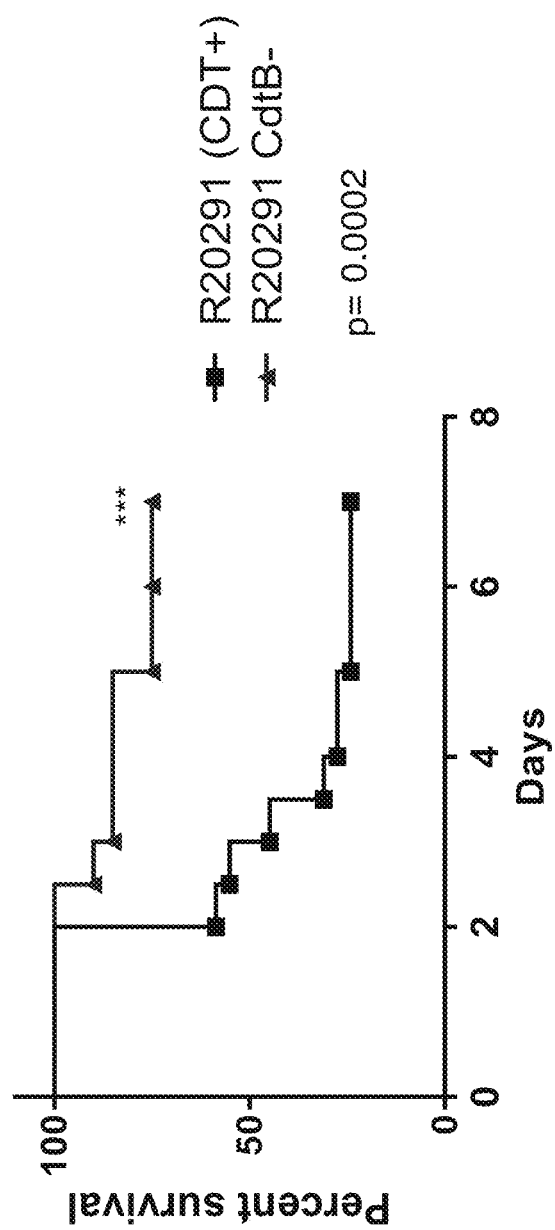
FIG. 2. CDT TOXIN INCREASES MORTALITY DURING CDI—Mice infected with *C. difficile* transferase toxin (CDT expressing *C. difficile*, strain R20291), have increased mortality compared to mice infected with isogenic mutant lacking CDT toxin and CDT toxin increases virulence of epidemic NAPI/027 strains of *C. difficile*—reproduced from Cowardin & Petri et al. *Nature Micr.*, 2016. Cowardin also showed (see Cowardin, FIG. 5E)

AAM—alternatively activated macrophage
ABX—antibiotic (also referred to as Abx)
aCDT—anti-CDT neutralizing nanobody
ARG1—arginase 1
aTLR2—anti-TLR2 neutralizing antibody
BMDC—bone marrow derived dendritic cells
*C. difficile*—*Clostridium difficile*
CDI—*Clostridium difficile* infection
CDT—*Clostridium difficile* transferase toxin
CFU—colony forming unit
Chil1—chitinase-like 1
EOP—eosinophil progenitor
FMT—fecal microbiota transplantation
kg—kilogram
IL1R2—interleukin 1 receptor type 2
IL4R—interleukin 4 receptor
IL-25—Interleukin 25
IL-33—Interleukin 33
LSR—lipolysis stimulated lipoprotein receptor
mg—milligram
µg—microgram
MMP8—matrix metallopeptidase 8
MMP10—matrix metallopeptidase 10
MSR1—macrophage scavenger receptor
ns—not significant
OTU—operational taxonomic unit
PBS—phosphate buffered saline
PRR—Pattern Recognition Receptor
rIL-25—recombinant IL-25
rIL-33—recombinant IL-33
SEAP—Secreted Embryonic Alkaline Phosphatase
Siglec-F—sialic acid-binding immunoglobulin-like lectin F
siRNA—small interfering RNA
STAT6—signal transducer and activator of transcription 6
TLR2—Toll-Like Receptor 2
T-reg—regulatory T cell
TSLP—thymic stromal lymphopoietin
UT—untreated
VPI 10463—a strain of *C. difficile*
YM-1—chitinase-like 3 (also referred to as Chil3)

Definitions

As used herein, the terms below are defined by the following meanings:

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

An "agent" useful for treating a *C. difficile* infection, as used herein means any compound, molecule, or cell that can directly or indirectly be used to treat an infection. Cells can include, for example, eosinophils or one or more types of bacteria. Such an "agent" can also be referred to as a "useful agent".

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both. A "therapeutic" treatment is a treatment administered to a subject who exhibits signs of pathology for the purpose of diminishing or eliminating those signs.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

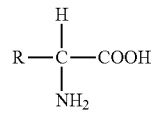

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6)

side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin subunit molecules. The antibodies in the present invention may exist in a variety of forms including, for example, polyclonal antibodies, monoclonal antibodies, Fv, Fab and F(ab)2, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "secondary antibody" refers to an antibody that binds to the constant region of another antibody (the primary antibody).

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

A pathology or symptom "associated" with *C. difficile* infection refers to mortality, colonic inflammation, diarrhea, weight loss, changes in expression and levels of genes, proteins, and cells as described herein or those that are known in the art that occur upon the infection or are a result of the infection.

The term "at least two antibiotics", as used herein, means at least two different antibiotics.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands. "Binding partner," as used herein, refers to a molecule capable of binding to another molecule.

The term "biological sample," as used herein, refers to samples obtained from a subject, including, but not limited to, skin, hair, tissue, blood, plasma, serum, cells, sweat, saliva, feces, tissue and/or urine.

As used herein, the term "biologically active fragments" or "bioactive fragment" of the polypeptides encompasses natural or synthetic portions of the full length protein that are capable of specific binding to their natural ligand or of performing the function of the protein. For example, a "functional" or "active" biological molecule is a biological molecule in a form in which it exhibits a property by which it is characterized. A functional enzyme, for example, is one which exhibits the characteristic catalytic activity by which the enzyme is characterized.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Co-administer" can include simultaneous and/or sequential administration of two or more agents.

A "compound," as used herein, refers to any type of substance or agent that is can be considered a drug, or a candidate for use as a drug, as well as combinations and mixtures of the above.

The terms "comprises", "comprising", and the like can have the meaning ascribed to them in U.S. Patent Law and can mean "includes", "including" and the like. As used herein, "including" or "includes" or the like means including, without limitation.

As used herein, the term "conservative amino acid substitution" is defined herein as an amino acid exchange within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln;
III. Polar, positively charged residues:
   His, Arg, Lys;
IV. Large, aliphatic, nonpolar residues:
   Met Leu, Ile, Val, Cys
V. Large, aromatic residues:
   Phe, Tyr, Trp "Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets, and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" generally means an amount which provides the desired local or systemic effect, such as enhanced performance. For example, an effective dose is an amount sufficient to affect a beneficial or desired clinical result. The dose could be administered in one or more administrations and can include any preselected amount. The precise determination of what would be considered an effective dose may be based on factors individual to each subject, including size, age, injury or disease being treated and amount of time since the injury occurred or the disease began. One skilled in the art, particularly a physician, would be able to determine what would constitute an effective dose.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

A "fragment" or "segment" is a portion of an amino acid sequence, comprising at least one amino acid, or a portion of a nucleic acid sequence comprising at least one nucleotide. The terms "fragment" and "segment" are used interchangeably herein. As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, at least about 100 to about 200 nucleotides, at least about 200 nucleotides to about 300 nucleotides, at least about 300 to about 350, at least about 350 nucleotides to about 500 nucleotides, at least about 500 to about 600, at least about 600 nucleotides to about 620 nucleotides, at least about 620 to about 650, and or the nucleic acid fragment will be greater than about 650 nucleotides in length.

As used herein, "health care provider" includes either an individual or an institution that provides preventive, curative, promotional, or rehabilitative health care services to a subject, such as a patient.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul [50; 1990]), modified as in Karlin and Altschul [51; 1993]. This algorithm is incorporated into the NBLAST and XBLAST programs of Altschul, et al. [52], and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. [53]. Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibiting TLR2" means to inhibit the activity, levels, or expression of TLR2 and is interpreted based on the context in which it is used. In one aspect, it refers to inhibiting its signaling activity by inhibiting it from binding with a ligand such as CDT. The term "inhibition of TLR2" when referring to a compound means that the compound is capable of "inhibiting TLR2".

As used herein "injecting or applying" includes administration of a compound of the invention by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide or antibody of the invention in the kit for diagnosing or effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The terms "intestinal microbiota", "gut flora", and "gastrointestinal microbiota" are used interchangeably to refer to bacteria in the digestive tract.

The term "isolated" refers to a compound, including antibodies, nucleic acids or proteins/peptides, or cell that has been separated from at least one component which naturally accompanies it.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

The term "microbiota" refers to an assemblage of microorganisms localized to a distinct environment.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

"Pharmaceutically acceptable" means physiologically tolerable, for either human or veterinary application.

As used herein, "pharmaceutical compositions" include formulations for human and veterinary use.

"Plurality" means at least two.

As used herein, the term "prebiotic" refers to an agent that increases the number and/or activity of one or more desired bacteria. Non-limiting examples of prebiotics useful in the methods of the present invention include fructooligosaccharides (e.g., oligofructose, inulin, inulin-type fructans), galactooligosaccharides, amino acids, alcohols, and mixtures thereof.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

As used herein, the term "probiotic" refers to a substantially pure bacteria (i.e., a single isolate), or a mixture of desired bacteria, and may also include any additional components that can be administered to a mammal for restoring microbiota. Such compositions are also referred to herein as a "bacterial inoculant." Probiotics or bacterial inoculant compositions of the invention are preferably administered with a buffering agent to allow the bacteria to survive in the acidic environment of the stomach, i.e., to resist low pH and to grow in the intestinal environment. Such buffering agents include sodium bicarbonate, milk, yogurt, infant formula, and other dairy products.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

The term "reduces recurrent infection" means that the number or percentage of subjects who get another C. difficile infection following a low dose or short-term course of treatment for an initial C. difficile infection is lower compared to the number who had received standard doses or standard duration therapies.

The term "regulate" refers to either stimulating or inhibiting a function or activity of interest.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

The term "standard," as used herein, refers to something used for comparison. For example, it can be a known standard agent or compound which is administered and used for comparing results when administering a test compound or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker. Standard can also refer to a healthy individual.

The term "stimulator of IL-33" as used herein means to stimulate or increase the expression, levels, or activity of IL-33 as described herein for treating C. difficile infection.

A "subject" is a vertebrate, including a mammal, such as a human. Mammals include, but are not limited to, humans, farm animals, sport animals, and pets.

A "subject in need thereof" is one who has been infected with C. difficile or who is in a high risk environment for C. difficile infection or is susceptible to a relapse of C. difficile infection. Based on the teachings of the present invention a clinician or other professional can determine if a preventive treatment may be necessary.

The term "substantially pure" describes a compound, e.g., a protein or polypeptide, cell or nucleic acid that has been separated from components which naturally accompany it. Typically, a compound is substantially pure when at least 10%, including at least 20%, at least 50%, at least 60%, at least 75%, at least 90%, at least 95%, at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

As used herein, a "substantially homologous amino acid sequences" or "substantially identical amino acid sequences" includes those amino acid sequences which have at least about 92%, or at least about 95% homology or identity, including at least about 96% homology or identity, including at least about 97% homology or identity, including at least about 98% homology or identity, and at least about 99% or more homology or identity to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" or "substantially identical nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In one embodiment, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 92%, 95%, 99% or more. Substantial identity of nucleic acid sequences can be determined by comparing the sequence identity of two sequences, for example by physical/chemical methods (i.e., hybridization) or by sequence alignment via computer algorithm.

Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; preferably in 7% (SDS), 0.5 M NaPO4, 1 mM EDTA at 50° C. with washing in 1×SSC, 0.1% SDS at 50° C.; preferably 7% SDS, 0.5 M NaPO4, 1 mM EDTA at 50° C. with washing in 0.5×SSC, 0.1% SDS at 50° C.; and more preferably in 7% SDS, 0.5 M NaPO4, 1 mM EDTA at 50° C. with washing in 0.1×SSC, 0.1% SDS at 65° C. Suitable computer algorithms to determine substantial similarity between two nucleic acid sequences include, GCS program package. The default settings provided with these programs are suitable for determining substantial similarity of nucleic acid sequences for purposes of the present invention.

By the term "susceptible to C. difficile infection", as used herein, refers to a subject who, due to a prior disease state, treatment, or condition has now become more susceptible to such an infection than if they had not had the prior disease, treatment, or condition. Such susceptible subjects are described herein and others are also known in the art.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, "treat," "treating", or "treatment" includes treating, ameliorating, or inhibiting an injury or disease related condition or a symptom of an injury or disease related condition. In one embodiment the disease, injury or disease related condition or a symptom of an injury or disease related condition is prevented; while another embodiment provides prophylactic treatment of the injury or disease related condition or a symptom of an injury or disease related condition. The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The present application provides compositions and methods useful for preventing or treating a Clostridium difficile (C. difficile) infection in a subject in need thereof. In one embodiment, the method comprises administering to the subject a pharmaceutical composition comprising a pharmaceutically-acceptable carrier, an effective amount of IL-33 or biologically active fragments or homologs thereof or an effective amount of a stimulator of IL-33. In one aspect, the composition further comprises an additional therapeutic agent. In one aspect, IL-33 is recombinant IL-33. In one aspect, the method increases survival of the subject. In one aspect, it protects against CDT induced mortality. In one aspect, the subject is treated before the infection as a preventative measure. In one aspect, the treatment reduces morbidity and mortality.

The present invention further encompasses agents or combinations of agents identified using the methods of the invention.

The invention further provides a method for preventing or treating a C. difficile infection. The method comprises administering to a subject in need thereof a pharmaceutical composition comprising an effective amount of one or more agents identified by the method described herein.

Clostridium difficile infection is a significant cause of antibiotic-associated nosocomial diarrhea. While discontinuation of the offending antibiotic is the ideal strategy to control the disease, in most cases, treatment with antimicrobial agents active against C. difficile is deemed necessary because of the severity of the gastrointestinal disease or the presence other active infections. Unfortunately, antimicrobial treatment for a first episode of CDI is associated with up to 25% recurrence of the disease. Alteration of the indigenous intestinal flora is critical to susceptibility to CDI and its recurrence. Antibiotic treatment may further disrupt the already abnormal flora and thereby enhance the growth of any leftover C. difficile organisms or of a newly acquired strain once antibiotics are discontinued.

It has been hypothesized that the intensity of the host response and resulting inflammation may be correlated with disease severity. Understanding and targeting host-based mediators of inflammation may provide a target for more effective therapy.

The present invention encompasses the use of IL-33 as a treatment for CDI. Useful IL-33 proteins, homologs, and fragments thereof include those with the activity described herein. Non-human IL-33 peptides with the activity described herein are also encompassed by the present invention. The invention further encompasses the use of recombinant IL-33 (rIL-33).

Some Useful IL-33 Peptides

SEQ ID NO:1—interleukin-33 isoform a precursor, *Homo sapiens*, NCBI Reference Sequence: NP_001300974.1, 270 amino acid residues MKPKMKYSTNKISTAKWKNTASKALCFKLGKSQQKAKEVCPMYFMKLRS
GLMIKKEACYFRRETTKRPSLKTGRKHKRHLVLAACQQQSTVECFAFGIS
GVQKYTRALHDSSITGISPITEYLASLSTYNDQSITFALEDESYEIYVED
LKKDEKKDKVLLSYYESQHPSNESGDGVDGKMLMVTLSPTKDFWLHANNK
EHSVELHKCEKPLPDQAFFVLHNMHSNCVSFECKTDPGVFIGVKDNHLAL
IKVDSSENLCTENILFKLSET SEQ ID NO:2 PREDICTED: interleukin-33 isoform X1, *Homo sapiens*, NCBI Reference Sequence: XP_016870774.1, 264 amino acid residues, (this is the same as interleukin-33 isoform d, NCBI Reference Sequence: NP_001300976.1)

MKPKMKYSTNKISTAKWKNTASKALCFKLGKSQQKAKEVCPMYFMKLRS
GLMIKKEACYFRRETTKRPSLKTGRKHKRHLVLAACQQQSTVECFAFGIS
GVQKYTRALHDSSITEYLASLSTYNDQSITFALEDESYEIYVEDLKKDEK
KDKVLLSYYESQHPSNESGDGVDGKMLMVTLSPTKDFWLHANNKEHSVEL
HKCEKPLPDQAFFVLHNMHSNCVSFECKTDPGVFIGVKDNHLALIKVDSS
ENLCTENILFKLSET

SEQ ID NO:3—PREDICTED: interleukin-33 isoform X2, *Homo sapiens*, NCBI Reference Sequence: XP_011516363.1, 229 amino acid residues MYFMKLRSGLMIKKEACYFRRETTKRPSLKTGRKHKRHLVLAACQQQSTV
ECFAFGISGVQKYTRALHDSSITGISPITEYLASLSTYNDQSITFALEDE
SYEIYVEDLKKDEKKDKVLLSYYESQHPSNESGDGVDGKMLMVTLSPTKD
FWLHANNKEHSVELHKCEKPLPDQAFFVLHNMHSNCVSFECKTDPGVFIG
VKDNHLALIKVDSSENLCTENILFKLSET SEQ ID NO:4—interleukin-33 isoform e, *Homo sapiens*, NCBI Reference Sequence: NP_001300977.1, 228 amino acid residues MKPKMKYSTNKISTAKWKNTASKALCFKLGKSQQKAKEVCPMYFMKLRS
GLMIKKEACYFRRETTKRPSLKTGISPITEYLASLSTYNDQSITFALEDE
SYEIYVEDLKKDEKKDKVLLSYYESQHPSNESGDGVDGKMLMVTLSPTKD
FWLHANNKEHSVELHKCEKPLPDQAFFVLHNMHSNCVSFECKTDPGVFIG
VKDNHLALIKVDSSENLCTENILFKLSET SEQ ID NO:5—interleukin-33 isoform b, *Homo sapiens*, NCBI Reference Sequence: NP_001186569.1, 228 amino acid residues MKPKMKYSTNKISTAKWKNTASKALCFKLGKSQQKAKEVCPMYFMKLRS
GLMIKKEACYFRRETTKRPSLKTGRKHKRHLVLAACQQQSTVECFAFGIS
GVQKYTRALHDSSITDKVLLSYYESQHPSNESGDGVDGKMLMVTLSPTKD
FWLHANNKEHSVELHKCEKPLPDQAFFVLHNMHSNCVSFECKTDPGVFIG
VKDNHLALIKVDSSENLCTENILFKLSET SEQ ID NO:6—interleukin-33 fragment, *Homo sapiens*, GenBank Accession No.: AOZ26495.1, 222 amino acid residues MKPKMKYSTNKISTAKWKNTASKALCFKLGSRKHKRHLVLAACQQQSTVE
CFAFGISGVQKYTRALHDSSITEYLASLSTYNDQSITFALEDESYEIYVE
DLKKDEKKDKVLLSYYESQHPSNESGDGVDGKMLMVTLSPTKDFWLHANN
KEHSVELHKCEKPLPDQAFFVLHNMHSNCVSFECKTDPGVFIGVKDNHLA
LIKVDSSENLCTENILFKLSET SEQ ID NO:7—interleukin-33 fragment, *Homo sapiens*, GenBank Accession No: AOZ26494.1, 180 amino acid residues MKPKMKYSTNKISTAKWKNTASKALCFKLGKYLASLSTYNDQSITFALED
ESYEIYVEDLKKDEKKDKVLLSYYESQHPSNESGDGVDGKMLMVTLSPTK
DFWLHANNKEHSVELHKCEKPLPDQAFFVLHNMHSNCVSFECKTDPGVFI
GVKDNHLALIKVDSSENLCTENILFKLSET SEQ ID NO:8—Novoprotein's recombinant IL-33, catalog # C091 (Uniprot Accession No. 095760). Recombinant Human Interleukin-33 is produced by their *E. coli* expression system and the target gene encoding Ser112-Thr270 (160 residues of the parent 270 residue peptide of Uniprot Accession No. 095760) is expressed. The sequence below is provided at the Novoprotein website associated with the catalog number and includes a methionine residue before serine 112.

MSITGISPITEYLASLSTYNDQSITFALEDESYEIYVEDLKKDEKKDKVL
LSYYESQHPSNESGDGVDGKMLMVTLSPTKDFWLHANNKEHSVELHKCEK
PLPDQAFFVLHNMHSNCVSFECKTDPGVFIGVKDNHLALIKVDSSENLCT
ENILFKLSET

SEQ ID NO:9—Origene's IL-33 human protein (Accession No. NM_033439), transcript variant 1, 159 amino acid residues, Cat. No. TP723227 (tag-free)

SITGISPITEYLASLSTYNDQSITFALEDESYEIYVEDLKKDEKKDKVLL
SYYESQHPSNESGDGVDGKMLMVTLSPTKDFWLHANNKEHSVELHKCEKP
LPDQAFFVLHNMHSNCVSFECKTDPGVFIGVKDNHLALIKVDSSENLCTE
NILFKLSET

SEQ ID NO:10—interleukin-33 isoform c, *Homo sapiens*, NCBI Reference Sequence: NP_001186570.1, 144 amino acid residues

```
MKPKMKYSTNKISTAKWKNTASKALCFKLGNKVLLSYYESQHPSNESGDG
VDGKMLMVTLSPTKDFWLHANNKEHSVELHKCEKPLPDQAFFVLHNMHS
NCVSFECKTDPGVFIGVKDNHLALIKVDSSENLCTENILFKLSET
```

SEQ ID NO:11—Interleukin 33, *Mus musculus*, GenBank: AAH03847.1, 266 amino acid residues

```
MRPRMKYSNSKISPAKFSSTAGEALVPPCKIRRSQQKTKEFCHVYCMRLRS
GLTIRKETSYFRKEPTKRYSLKSGTKHEENFSAYPRDSRKRSLLGSIQAFA
ASVDTLSIQGTSLLTQSPASLSTYNDQSVSFVLENGCYVINVDDSGKDQEQ
DQVLLRYYESPCPASQSGDGVDGKKVMVNMSPIKDTDIVVLHANDKDYSVE
LQRGDVSPPEQAFFVLHKKSSDFVSFECKNLPGTYIGVKDNQLALVEEKDE
SCNNIMFKLSKI
```

SEQ ID NO:12—*Mus musculus*, 158 amino acid residue peptide comprising residues Ser109-Ile266 of SEQ ID NO:11.

```
SIQGTSLLTQSPASLSTYNDQSVSFVLENGCYVINVDDSGKDQEQDQVLLR
YYESPCPASQSGDGVDGKKVMVNMSPIKDTDIWLHANDKDYSVELQRGDVS
PPEQAFFVLHKKSSDFVSFECKNLPGTYIGVKDNQLALVEEKDESCNNIMF
KLSKI
```

One of ordinary skill in the art will appreciate that, based on the teachings herein, the dose of IL-33 (or biologically active fragments and homologs thereof) can be varied depending on such things as the age, health, sex, and age of the subject as well as the severity of the CDI or whether it is being used as a preventative. For example, mice received 0.5 μg to 1.25 μg of recombinant IL-33 intraperitoneally daily for 5 days prior to infection or for various amounts of time. Considering that mice can range from 20 to 30 grams, calculations for ranges and unit doses can be extrapolated to humans. For example, if a mouse is approximately 20 grams in weight, when this dose is translated to humans, the dose would be approximately 25 μg of rIL-33/kg body weight to about 62.5 μg of rIL-33/kg body weight. Additionally, depending on various parameters regarding the subject, whether a dose is provided in one administration to a subject or as multiples, the present invention further encompasses doses of about 1.0 ug/kg body weight to about 500 μg/kg body weight. In one aspect, the range is about 2.0 to about 150 μg IL-33/kg body weight. In another aspect, the range is about 5.0 to about 100 μg/kg body weight. In yet another aspect, the dose range is about 10 to about 75 μg/kilo body weight. In a further aspect, the range is about 20 to about 50 μg/kg body weight. The doses include fractions and decimals of the doses provided herein. In one aspect, the therapeutically effective dose used is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 58, 59, 60, 61, 62, 62.5, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 μg IL-33/kg body weight, and decimals thereof. The total amount to be administered during a day can be divided into lower doses and administered at multiple times/day. In one aspect, the method is useful for low dose treatment.

In one embodiment, a dose of about 0.5-250 μg/kg of recombinant IL-33 is administered daily for 5 days may be effective at reducing CDI-associated mortality rates in humans. In one aspect, it is administered for 1, 2, 3, 4, 5, 6, 7, 8, 9, or 10 days. Alternatively, a single dose of about 1.0 to about 1,250 μg/kg of recombinant IL-33 administered only once may be effective at reducing CDI-associated mortality rates in humans as well as the other signs resulting from CDI.

In one embodiment, a dose can be about 0.01 μg per 20 grams body weight to about 100 μg per 20 grams body weight. In one embodiment, a dose can be about 0.1 μg per 20 grams body weight to about 50 μg per 20 grams body weight. In one embodiment, a dose can be about 0.5 μg per 20 grams body weight to about 25 μg per 20 grams body weight. In one embodiment, a dose can be about 1.0 μg per 20 grams body weight to about 15 μg per 20 grams body weight. In one embodiment, a dose can be about 1.25 μg per 20 grams body weight to about 10 μg per 20 grams body weight. In one aspect, a dose can be about 1.25 μg per 20 grams body weight and in another aspect, about 1.25 μg per 30 grams body weight.

In one embodiment, a dose of IL-33, or a biologically active fragment or homolog thereof can be about 0.01 μg per 30 grams body weight to about 100 μg per 30 grams body weight. In one embodiment, a dose can be about 0.1 μg per 30 grams body weight to about 50 μg per 30 grams body weight. In one embodiment, a dose can be about 0.5 μg per 30 grams body weight to about 25 μg per 30 grams body weight. In one embodiment, a dose can be about 0.75 μg per 30 grams body weight to about 20 μg per 30 grams body weight. In one embodiment, a dose can be about 1.0 μg per 30 grams body weight to about 15 μg per 30 grams body weight. In one embodiment, a dose can be about 1.25 μg per 30 grams body weight to about 10 μg per 30 grams body weight.

In one embodiment, when an antibiotic is also being used and depending on the particular antibiotic being administered and the route of administration, the dose ranges from about 0.1 mg/kg/day to about 20 mg/kg/day. In one embodiment, the dose is selected from the group consisting of 0.1, 0.5, 1.0, 1.5, 2.0, 2.5, 3.0, 3.5, 4.0, 4.5, 5.0, 6.0, 7.0, 8.0, 9.0, and 10.0, 11.0, 12.0, 13.0, 14.0, 15.0, 16.0, 17.0, 18.0, 19.0, and 20.0 mg/kg/day.

In one embodiment, duration of treatment is from about 1-10, 1-9, 1-8, 1-7, 1-6, 1-5, 1-4, 1-3, or 1-2 days. In one aspect, duration of treatment is from about 2-10, 2-9, 2-8, 2-7, 2-6, 2-5, 2-4, or 2-3 days. In one aspect, duration of treatment is from about 3-10, 3-9, 3-8, 3-7, 3-6, 3-5, or 3-4 days. In one aspect, duration of treatment is from about 4-10, 4-9, 4-8, 4-7, 4-6, or 4-5 days. In one aspect, duration of treatment is from about 5-10, 5-9, 5-8, 5-7, or 5-6 days. In one aspect, duration of treatment is from about 6-10, 6-9, 6-8, or 6-7 days. In one aspect, duration of treatment is from about 7-10, 7-9, or 7-8 days. In one aspect, duration of treatment is from about 8-10 or 8-9.

In one embodiment, treatment is for about 1, 2, 3, 4, 5, 6, 7, 8, 9, or 10 days.

In one embodiment, a subject is treated daily during the treatment regimen when the duration is longer than one day. In another aspect, the subject is treated every other day.

One of ordinary skill in the can determine the method and site of administration. For example, enteral, parental, direct, intravenous, or subcutaneous injection of IL-33 protein (or biologically active fragments or homologs thereof) would be an effective treatment.

In one embodiment, for short durations of treatment the present invention provides a dosage range of at least one antibiotic of the invention of about 0.1 mg/kg to about 75 mg/kg. In one aspect, it is from about 0.5 to about 50 mg/kg. In another aspect, it is from about 2.0 to about 40 mg/kg. In yet another aspect, it is from about 3.0 to about 35 mg/kg. In another aspect, it is from about 4.0 to about 30 mg/kg. In a further aspect, it is from about 5.0 to about 25 mg/kg. In another aspect, it is from about 6.0 to about 20 mg/kg. In a further aspect, it is from about 7.0 to about 15 mg/kg. In one aspect, the dose is about 0.1, 0.5, 1.0, 2.0, 3.0, 4.0, 5.0, 6.0, 7.0, 8.0, 9.0, 10, 15, 20, 25, 30, 32, 35, 40, 45, 55, 60, 65, 70, or about 75 mg/kg. One of ordinary skill in the art can determine which dose to use depending on whether the treatment is for a short duration, or for a low dose, or a combination of the two. In one aspect, a short-term treatment such as 1 or 2 days may use a slightly higher dose than a treatment that lasts longer.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" unless stated otherwise.

The total amount to be administered during a day can be divided into lower doses and administered at multiple times/day. In one aspect, the method is useful for low dose treatment. In one aspect, the method is useful for short-term treatment. For example, if 20 mg/kg/day is the prescribed amount for the day, that amount can be divided into more than one dose for administration during the day, such as doses of 10 mg/kg administered twice. In one embodiment, treatment can be as short as 1 day. In a further embodiment, even doses as low as 0.01, 0.1, 0.5, 1.0, 1.5, 2.0, 2.5, 3.0, 3.5, 4.0, 4.5, and 5.0 mg/kg/day can be administered as partial doses multiple times in a day when it is determined that the entire daily dose does not need to be administered in one bolus or that it would be better to administer the daily dose in several increments.

When two or more compounds are to be administered, they can be administered in the same pharmaceutical composition or in separate pharmaceutical compositions. When administered in separate pharmaceutical compositions, they can be administered simultaneously or one can be administered first. The amount of time between administration of the different compounds can vary and can be determined by one of ordinary skill in the art. For example, the two compounds could be administered up to 10 minutes apart, up to 30 minutes apart, up to 1 hour apart, etc. In one aspect, one or more of the compounds can be administered more than once. In one aspect, a compound is administered at least twice. In another aspect, a compound is administered at least five times. In one aspect, the method is useful for low dose treatment. In one aspect, the method is useful for short-term treatment.

An effective dose as described herein is, in one aspect, one that is sufficient to treat infection and control diarrhea and weight loss in a subject infected with *C. difficile*. Moreover, with this strategy, the intestinal gut flora is preserved and recurrent disease is prevented. Immunologic studies reveal that with standard doses of antibiotics, IgG production is reduced. It is disclosed herein that mice treated with low dose anti-*C. difficile* agents had higher IgG levels than those treated with high dose.

In one aspect, an effective dose reduces mortality.

In one aspect, the compositions and methods of the invention are useful for preventing relapse in an already treated subject and in preventing reinfection.

One of ordinary skill in the art can determine the best route of administration of a pharmaceutical composition of the invention. For example, administration can be direct, enteral, or parenteral. Enteral includes, for example, oral and rectal administration. Parenteral includes, for example, intravenous administration.

A compound of the invention can be administered once or more than once. It can be administered once a day or at least twice a day. In one aspect, a compound is administered every other day within a chosen term of treatment. In one embodiment, at least two compounds of the invention are used. One of ordinary skill in the art can determine how often to administer a compound of the invention, the duration of treatment, and the dosage to be used.

Treatment of CDI as described herein is useful for prevention of relapse or reinfection, as well as reducing the frequency of relapse or reinfection.

In one embodiment, the present invention provides compositions and therapeutic methods involving the use of probiotics, prebiotics, or narrow spectrum antibiotics/antibacterial agents that are capable of restoring healthy mammalian bacterial gastrointestinal microbiota.

When two or more compounds are to be administered, they can be administered in the same pharmaceutical composition or in separate pharmaceutical compositions. When administered in separate pharmaceutical compositions, they can be administered simultaneously or one can be administered first. The amount of time between administration of the different compounds can vary and can be determined by one of ordinary skill in the art. For example, the two compounds could be administered up to 10 minutes apart, up to 30 minutes apart, up to 1 hour apart, etc. In one aspect, one or more of the compounds can be administered more than once. In one aspect, a compound is administered at least twice. In another aspect, a compound is administered at least five times. In one aspect, the method is useful for low dose treatment. In one aspect, the method is useful for short-term treatment.

The compounds of the present invention can be further combined with growth factors, nutrient factors, pharmaceuticals, calcium-containing compounds, anti-inflammatory agents, antimicrobial agents, or any other substance capable of expediting or facilitating the treatment.

In one embodiment, an effective dose as described herein is, in one aspect, one that is sufficient to prevent treat infection and control diarrhea and weight loss in a subject infected with *C. difficile*. Moreover, with this strategy, in one aspect, the intestinal gut flora is preserved and recurrent disease is prevented.

In one aspect, an effective dose reduces mortality.

In one aspect, the compositions and methods of the invention are useful for preventing relapse in an already treated subject and in preventing reinfection.

In one aspect, doses are preventive.

In one embodiment, targeted restoration of the intestinal microbiota is used to prevent or treat relapsing *C. difficile* infection or increase resistance to infection (see Lawley et al., PLOS Pathogens, 2012 and Buffie et al., Nature, 2015). In one aspect, these treatments can be used in conjunction with other therapies disclosed herein. The present invention provides for targeting a dysbiotic microbiota with a defined mixture of diverse bacteria to change the microbial community in the intestine such that it displaces *C. difficile* or is resistant to *C. difficile*. In one embodiment, useful bacteria include those that induce IL-33 when administered to a subject. In one embodiment, useful bacteria include those that are protective against *C. difficile*. Useful bacteria for the methods of the invention include, but are not limited to, *Clostridium scindens, C. populati, C. vincentii, C. irregulare, Blautia hansenii, Eubacterium contortum, Ruminococcus torques, Pseudoflavonifractor capillosus, Anaerostipes* sp., *Staphylococcus warneri, Lactobacillus reuteri, Enterococcus hirae, Enterorhabdus* sp. *nov.*, and *Bacteroidetes* sp. *nov.* For example, *Clostridium scindens, C. populati, C. vincentii, C. irregulare, Blautia hansenii, Eubacterium contortum, Ruminococcus torques*, and *Pseudoflavonifractor capillosus* were shown to be protective by Buffie et al., (2015, Nature). Also, *Anaerostipes* sp., *Staphylococcus warneri, Lactobacillus reuteri, Enterococcus hirae, Enterorhabdus* sp. *nov.*, and *Bacteroidetes* sp. *nov.* were shown to be useful for restoration of the microbiota by Lawley et al. (PLOS Pathogens, 2012).

In one embodiment, the present invention provides compositions and methods for treating *C. difficile* infections by regulating the microbiota of the gut. In one aspect, the invention provides a method of treatment comprising administering to the subject a therapeutically effective amount of a probiotic composition comprising one or more bacterial strains, wherein the composition stimulates the growth or activity of one or more bacterial taxa which are under-represented in microbiota of the mammal as compared to a healthy control or inhibits the growth or activity of one or more bacterial taxa which are over-represented in microbiota of the mammal as compared to a healthy control. In one aspect, the treatment induces IL-33 signaling, expression, levels, or activity.

The present invention provides for treating CDI to reduce infection and to increase survival of subjects being treated.

In one embodiment of the invention, a fecal sample or microbiota derived from a fecal sample is used to treat a subject in need thereof. In one aspect, the fecal sample is from a subject not infected with *C. difficile*. In one aspect, one or more bacteria species derived from a fecal sample are used.

Various bacteria can be used, for example, *H. pylori, Lactobillus* species, and *Oxalobacter* species.

Bacterial strains administered according to the methods of the present invention can comprise live bacteria. One or several different bacterial inoculants can be administered simultaneously or sequentially (including administering at different times). Such bacteria can be isolated from microbiota and grown in culture using known techniques. However, many bacterial species are very difficult to culture and administration of others (like *H. pylori*) may lead to various undesirable side-effects. The present invention therefore comprises administering "bacterial analogues", such as recombinant carrier strains expressing one or more heterologous genes derived from the bacteria affected in a disease. The use of such recombinant bacteria may allow the use of lower therapeutic amounts due to higher protein expression and may simultaneously avoid any potential harmful side-effects associated with reintroduction of specific bacterial strains. Non-limiting examples of recombinant carrier strains useful in the methods of the present invention include *E. coli* and *Lactobacillus* (e.g., *E. coli* and Lactobacillus expressing cag island-encoded type IV secretion system of *H. pylori*). Methods describing the use of bacteria for heterologous protein delivery are described, e.g., in U.S. Pat. No. 6,803,231.

Human fecal material is screened for the presence of pathogenic microorganisms prior to its use.

Fecal samples have been used, for example, to treat *C. difficile* colitis (Hlavka, U.S. Pat. Pub. No. U.S. 2014/0086877, published Mar. 27, 2014).

Administration of a bacterial inoculant can be accomplished by any method likely to introduce the organisms into the desired location. The bacteria can be mixed with a carrier and (for easier delivery to the digestive tract) applied to liquid or solid food or to drinking water. The carrier material should be non-toxic to the bacteria and the subject/patient. Preferably, the carrier contains an ingredient that promotes viability of the bacteria during storage. The formulation can include added ingredients to improve palatability, improve shelf-life, impart nutritional benefits, and the like. If a reproducible and measured dose is desired, the bacteria can be administered by a rumen cannula.

The dosage of the bacterial inoculant or compound of the invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization of the gastrointestinal tract with the desired bacterial inoculant, e.g. about $10^6$, $10^7$, $10^8$, $10^9$, and $10^{10}$ CFU for example. The dose can be administered as a single dose. In one embodiment, lower doses can be effective, including, but not limited to, about $10^3$, $10^4$, and $10^5$ CFU.

In certain embodiments, a conditional lethal bacterial strain can be utilized as the inoculant or to deliver a recombinant construct. Such a conditional lethal bacteria survives for a limited time typically when provided certain nutritional supplements. It is contemplated that such a supplement could be a liquid, formulated to contain the nutritional component necessary to keep the bacteria alive. It is further contemplated that a patient/subject would drink such a supplement in intervals to keep the bacteria alive. Once the supplement is depleted, the conditional lethal bacteria die. Methods relating to conditional lethal strains of *H. pylori* are described in U.S. Pat. No. 6,570,004.

A compound of the invention can be administered once or more than once. It can be administered once a day or at least twice a day. In one aspect, a compound is administered every other day within a chosen term of treatment. In one embodiment, at least two compounds of the invention are used.

One of ordinary skill in the art can determine how often to administer a compound of the invention, the duration of treatment, and the dosage to be used. Factors used in such a determination include the severity of the infection, the age and health of the subject, the particular anti-*C. difficile* antibiotic being administered, and the route of administration.

Treatment of CDI as described herein is useful for prevention of relapse or reinfection, as well as reducing the frequency of relapse or reinfection.

One of ordinary skill in the art can determine the dose and term of treatment to be used.

When two or more compounds are to be administered, they can be administered in the same pharmaceutical composition or in separate pharmaceutical compositions. When administered in separate pharmaceutical compositions, they can be administered simultaneously or one can be administered first. The amount of time between administration of the different compounds can vary and can be determined by one of ordinary skill in the art. For example, the two compounds could be administered up to 10 minutes apart, up to 30 minutes apart, up to 1 hour apart, etc. In one aspect, one or more of the compounds can be administered more than once. In one aspect, a compound is administered at least twice. In another aspect, a compound is administered at least five times. In one aspect, the method is useful for low dose treatment. In one aspect, the method is useful for short-term treatment.

An effective dose as described herein is, in one aspect, one that is sufficient to treat infection and control diarrhea and weight loss in a subject infected with *C. difficile*. Moreover, with this strategy, the intestinal gut flora is preserved and recurrent disease is prevented.

In one aspect, an effective dose reduces mortality.

In one aspect, the compositions and methods of the invention are useful for preventing relapse in an already treated subject and in preventing reinfection.

One of ordinary skill in the art can determine the best route of administration of a pharmaceutical composition of the invention. For example, administration can be direct, enteral, or parenteral. Enteral includes, for example, oral and rectal administration. Parenteral includes, for example, intravenous administration.

The present invention further encompasses the use of therapeutically active homologs, analogs, and derivatives of the useful compounds of the invention.

The present invention further provides for the use of a unit dose.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" unless stated otherwise.

In one embodiment, at least one compound of the invention can be administered in conjunction with another therapeutic agent. Additional therapeutic agents include, for example, antibiotics, anti-diarrheals, steroids, anti-inflammatories, other antimicrobials, and inducers of chemokines. In one aspect, more than one therapeutic agent can be administered in conjunction with a therapeutic compound of the invention. Other antimicrobials include those drugs useful against infection other than a *C. diff.* infection where a subject may have need for treatment against an additional infection as well.

The present invention further provides kits comprising compounds of the invention, an applicator, and an instructional material for the use thereof.

Diarrhea

Inflammatory diarrhea occurs when there is damage to the intestinal mucosal lining or brush border, which leads to a passive loss of protein-rich fluids, and a decreased ability to absorb these lost fluids. Features of all three of the other types of diarrhea can be found in this type of diarrhea. It can be caused by bacterial infections, viral infections, parasitic infections, or autoimmune problems such as inflammatory bowel diseases. It can also be caused by tuberculosis, colon cancer, and enteritis.

Inflammatory diarrheas include those caused by enteric pathogens including, but not limited to, *Campylobacter jejuni, Salmonella* species, *Shigella* species, *Escherichia coli* (including enterohemorrhagic, enterotoxigenic, enteroaggregative *E. coli*), *Entamoeba histolytica, Clostridium difficile, Cryptosporidium* and those that have no clearly defined infectious agent such as, Crohn's Disease (CD) and ulcerative colitis (UC).

*Clostridium difficile* antibiotic-associated colitis is an increasing problem in health-care associated diarrhea, made more so recently by the emergence of a quinolone-resistant hyper-virulent strain. The infection is potentially fatal, difficult to treat, and prone to relapse.

Infectious diarrhea or contagious diarrhea may be defined as diarrhea caused by an infection of the digestive system by a bacterium, virus, or parasite that result in frequent bowel motions producing liquid feces. Viral diarrheas include, but are not limited to, those caused by *Norovirus, Rotavirus, Adenovirus,* or *Astrovirus*. Bacterial diarrheas, including diarrheas caused by their toxins, include, but are not limited to, diarrhea caused by *Campylobacter jejuni, Salmonella, Shigella, Vibrio cholerae/Cholera, Vibrio parahaemolyticus, Escherichia coli* (including enterohemorrhagic, enterotoxigenic, enteroaggregative *E. coli*), *Clostridium difficile,* staphylococcal toxin and *Bacillus cereus*.

Antimicrobials are substances that kill or inhibit the growth of microorganisms such as bacteria, fungi, virus, or protozoans. Antimicrobial drugs either kill microbes (microbiocidal) or prevent the growth of microbes (microbiostatic).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices. For example, the active compound can be formulated to release only in the intestine and/or the colon.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the compounds of the invention can be determined by comparing their in vitro activity and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary with the route of administration, the nature of the condition being treated and the age and condition of the patient and will be ultimately at the discretion of the attendant physician or clinician.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

Aptamers

The present invention is also directed to useful aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

Other assays and libraries are encompassed within the invention, such as the use of Phylomers® and reverse yeast two-hybrid assays (see Watt, 2006, Nature Biotechnology, 24:177; Watt, U.S. Pat. No. 6,994,982; Watt, U.S. Pat. Pub. No. 2005/0287580; Watt, U.S. Pat. No. 6,510,495; Barr et al., 2004, J. Biol. Chem., 279:41:43178-43189; the contents of each of these publications is hereby incorporated by reference herein in their entirety). Phylomers® are derived from sub domains of natural proteins, which makes them potentially more stable than conventional short random peptides. Phylomers® are sourced from biological genomes that are not human in origin. This feature significantly enhances the potency associated with Phylomers® against human protein targets. Phylogica's current Phylomer® library has a complexity of 50 million clones, which is comparable with the numerical complexity of random peptide or antibody Fab fragment libraries. An Interacting Peptide Library, consisting of 63 million peptides fused to the B42 activation domain, can be used to isolate peptides capable of binding to a target protein in a forward yeast two hybrid screen. The second is a Blocking Peptide Library made up of over 2 million peptides that can be used to screen for peptides capable of disrupting a specific protein interaction using the reverse two-hybrid system.

The Phylomer® library consists of protein fragments, which have been sourced from a diverse range of bacterial genomes. The libraries are highly enriched for stable subdomains (15-50 amino acids long). This technology can be integrated with high throughput screening techniques such as phage display and reverse yeast two-hybrid traps.

The present application discloses compositions and methods for regulating the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides.

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), diinethylene-sulfoxide (—CH2-SO—CH2), dimethylene-sulfone (—CH2-SO2-CH2), 2'-O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nuleic: acids can be purified by reverse phase or ion exchange HPLC, size exclusion chromatography or gel electrophoresis. Of course, the skilled artisan will recognize that the method of purification will depend in part on the size of the DNA to be purified. The term nucleic acid also specifically includes nucleic acids composed of bases other than the five biologically occurring bases (adenine, guanine, thymine, cytosine and uracil).

The present invention also encompasses pharmaceutical and therapeutic compositions comprising the compounds of the present invention.

The present invention is also directed to pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art.

When used in vivo for therapy, the proteins or biologically active fragments or homologs thereof of the invention are administered to the subject in therapeutically effective amounts (i.e., amounts that have a desired therapeutic effect). In one aspect, they will be administered parenterally.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without effect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

Antibodies and Their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

In one embodiment, antibodies, or antisera, directed against TLR2 or a homolog or fragment thereof, are useful for blocking the activity of TLR2.

Fragments of TLR2 may be generated and antibodies prepared against the fragments. Assays are provided herein to determine whether an antibody directed against TLR2, or a fragment thereof, have the ability to detect TLR2, to inhibit TLR2 activity, or regulate TLR2 function.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals.

In one embodiment, the monoclonal antibodies described herein and the hybridomas making the antibodies, as well as those not described herein, will be deposited with the American Type Culture Collection (10801 University Boulevard, Manassas, Va. 20110-2209) and assigned Accession Numbers. The deposits will be maintained under the terms of the Budapest Treaty on the International Recognition of the Deposit of Microorganisms for the Purposes of Patent Procedure and made available for use under those terms. This assures maintenance of a viable culture of the deposit for 30 years from the date of deposit. The deposits will be made available by ATCC under the terms of the Budapest Treaty, and subject to an agreement between the University of Virginia and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC section 122 and the Commissioner's rules pursuant thereto (including 37 CFR section 1.14 with particular reference to 886 OG 638). The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws. Nucleic acid and amino acid sequences will be deposited with GenBank and made accessible to the public.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of TLR2 polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in *Solid Phase Peptide Synthesis*, 2nd Edition, 1984, Pierce Chemical Company, Rockford, Ill.; and as described by Bodanszky and Bodanszky in *The Practice of Peptide Synthesis*, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method that utilized tert-butyloxycarbonyl as the α-amino protecting group, and the FMOC method which utilizes 9-fluorenylmethyloxycarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As used herein, an antagonist or inhibiting agent may comprise, without limitation, a drug, a small molecule, an antibody, an antigen binding portion thereof or a biosynthetic antibody binding site that binds a particular target protein; an antisense molecule that hybridizes in vivo to a nucleic acid encoding a target protein or a regulatory element associated therewith, or a ribozyme, aptamer, or small molecule that binds to and/or inhibits a target protein, or that binds to and/or inhibits, reduces or otherwise modulates expression of nucleic acid encoding a target protein.

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other cellular proteins. Such screening assays will include assays amenable to high-throughput screening of chemical libraries, making them particularly suitable for identifying small molecule drug candidates.

When used in vivo for therapy, the antibodies of the subject invention are administered to the subject in therapeutically effective amounts (i.e., amounts that have desired therapeutic effect). They will normally be administered parenterally. The dose and dosage regimen will depend upon the degree of the infection, the characteristics of the particular antibody or immunotoxin used, e.g., its therapeutic index, the patient, and the patient's history. Advantageously the antibody or immunotoxin is administered continuously over a period of 1-2 weeks. Optionally, the administration is made during the course of adjunct therapy such as antimicrobial treatment, or administration of tumor necrosis factor, interferon, or other cytoprotective or immunomodulatory agent.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Antimicrobial agents include, but are not limited to, antibacterial, antifungal, and antiviral agents. For example, antimicrobial agents include silver sulfadiazine, nystatin, nystatin/triamcinolone, bacitracin, nitrofurazone, nitrofurantoin, a polymyxin, doxycycline, antimicrobial peptides, beosporin, polysporin, silver salts, iodine, benzalkonium chloride, alcohol, hydrogen peroxide, and chlorhexidine.

Examples of other antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

In one embodiment, the compounds of the invention can first be encapsulated into microcapsules, microspheres, microparticles, microfibers, reinforcing fibers and the like to facilitate mixing and achieving controlled, extended, delayed and/or sustained release and combined other agents or drugs. Encapsulating the biologically active agent can also protect the agent against degradation during formation of the composite of the invention.

In another embodiment of the invention, the compound is controllably released into a subject when the composition of the invention is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

For parenteral administration, the antibodies will be formulated in a unit dosage injectable form (solution, suspension, emulsion) in association with a pharmaceutically acceptable parenteral vehicle. Such vehicles are inherently nontoxic, and non-therapeutic. Examples of such vehicle are water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability, e.g., buffers and preservatives. The antibodies will typically be formulated in such vehicles at concentrations of about 1.0 mg/ml to about 10 mg/ml.

Use of IgM antibodies can be preferred for certain applications; however, IgG molecules by being smaller can be more able than IgM molecules to localize to certain types of infected cells.

There is evidence that complement activation in vivo leads to a variety of biological effects, including the induction of an inflammatory response and the activation of macrophages (Unanue and Benecerraf, Textbook of Immunology, 2nd Edition, Williams & Wilkins, p. 218 (1984)). The increased vasodilation accompanying inflammation can increase the ability of various agents to localize. Therefore, antigen-antibody combinations of the type specified by this invention can be used in many ways. Additionally, purified antigens (Hakomori, Ann. Rev. Immunol. 2:103, 1984) or anti-idiotypic antibodies (Nepom et al., Proc. Natl. Acad. Sci. USA 81: 2864, 1985; Koprowski et al., Proc. Natl. Acad. Sci. USA 81: 216, 1984) relating to such antigens could be used to induce an active immune response in human patients.

The antibody compositions used are formulated and dosages established in a fashion consistent with good medical practice taking into account the condition or disorder to be treated, the condition of the individual patient, the site of delivery of the composition, the method of administration, and other factors known to practitioners.

The present application discloses compositions and methods for inhibiting the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides, as well as the protein itself and fragments thereof.

The present invention further encompasses the identification of functional fragments for the use of TLR2 for use as antigens for therapeutic antibodies as well as its use as an immunogen and vaccine.

The present invention is also directed to pharmaceutical compositions comprising the compounds of the present invention. More particularly, such compounds can be formulated as pharmaceutical compositions using standard pharmaceutically acceptable carriers, fillers, solubilizing agents and stabilizers known to those skilled in the art.

In accordance with one embodiment, a method of treating a subject in need of treatment is provided. The method comprises administering a pharmaceutical composition comprising at least one compound of the present invention to a subject in need thereof. Compounds identified by the methods of the invention can be administered with known compounds or other medications as well.

The invention also encompasses the use of pharmaceutical compositions of an appropriate compound, and homologs, fragments, analogs, or derivatives thereof to practice the methods of the invention, the composition comprising at least one appropriate compound, and homolog, fragment, analog, or derivative thereof and a pharmaceutically-acceptable carrier.

In one embodiment, the pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 µg to about 100 g per kilogram of body weight of the subject. While the precise dosage administered will vary depending upon any number of factors, including, but not limited to, the type of animal and type of disease state being treated, the age of the subject and the route of administration. In one aspect, the dosage of the compound will vary from about 1 mg to about 10 g per kilogram of body weight of the subject. In another aspect, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the condition or disease being treated, the type and age of the subject, etc.

The invention is also directed to methods of administering the compounds of the invention to a subject. In one embodiment, the invention provides a method of treating a subject by administering compounds identified using the methods of the invention. Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate, and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group.

Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines ($-NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without effect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

Regulating TLR2 Pathways (see Cowardin et al., 2016, Nature Microbiology, 1:8:16108, doi:10.1038/nmicrobiol.2016.108, "The binary toxin CDT enhances *Clostridium difficile* virulence by suppressing protective colonic eosinophilia", the entirety of which is incorporated by reference herein).

The TLR2 pathways can be regulated in conjunction with the regulation of the IL-33 pathway as disclosed herein.

In one embodiment, the present invention provides compositions and methods for preventing or treating *C. difficile* infection comprising administering inhibitors of Toll-like Receptor 2 (TLR2) and its dependent pathway in subjects infected with *C. difficile* strains that produce CDT. In one aspect, inhibitors of TLR2 are administered to a subject in need thereof. Inhibitors include, but are not limited to, those that inhibit levels, expression, and activity of TLR2. Inhibition of activity can also include inhibiting its downstream signaling and pathways. The inhibitors can act directly on TLR2 or can, for example, inhibit its interaction with its ligand. The inhibitors include, but are not limited to, antibodies, fragments of antibodies, humanized antibodies, monoclonal antibodies, aptamers, phylomers, antisense oligonucleotides, nucleic acids, siRNA, proteins, other biologics, and drugs.

In one embodiment, the inhibitor binds to TLR2. In one aspect, it prevents TLR2 from interacting with its ligand. In one aspect, it inhibits TLR2 activity.

The compositions and methods of the invention are useful for inhibiting the effects of CDT, including, reducing its ability to stimulate host inflammatory signaling, inhibiting its enhancement of virulence of certain *C. diff.* strains, inhibiting its suppression of protective colonic eosinophilia, and inhibiting its promotion of apoptosis of eosinophils.

In one embodiment, an inhibitor of TLR2 is administered in combination with an agent that binds with CDT, wherein the agent that binds to CDT inhibits the interaction of CDT with its target or inhibits CDT activity.

In one embodiment, an inhibitor of CDT activity is administered. The inhibitor can include, but is not limited to, antibodies, vaccines, and chemicals.

In one embodiment, inhibiting CDT inhibits its ability to increase virulence of certain *C. difficile* strains.

In one embodiment, the present invention provides for the use of TLR2-deficient eosinophils to treat or prevent *C. difficile* infection. TLR2-deficient eosinophils can be prepared, for example, using gene-editing technology. Stem or progenitor cells with the ability to give rise to eosinophils can be subjected to gene editing to produce TLR2-deficient cells and then expanded/differentiated to produce sufficient cells for administering to the subject or can be administered such that they will expand and/or differentiate once administered. In one aspect, eosinophils can be subjected to the gene editing. In one aspect, the cells are derived from the subject.

As demonstrated in Cowardin et al. and in U.S. patent application Ser. No. 15/597,384, in one embodiment, *C.*

*difficile* infection can be prevented or treated using a combination treatment comprising administration of TLR2-deficient eosinophils or TLR2-deficient eosinophil precursors and at least one inhibitor of TLR2. In one embodiment, an inhibitor of CDT can also be administered. Therefore, the present invention encompasses the use of IL-33 in combination with administering regulators of TLR-2.

The present invention provides antibodies useful for identifying and monitoring TLR2 expression levels and expression. The present invention provides antibodies useful for inhibiting CDT induced activity of TLR2 and for inhibiting TLR2. There are multiple commercial sources for these antibodies including Invivogen, Abcam, ThermoFisher, and R&D Systems. Useful Invivogen antibodies include: 1) Anti-hTLR2-IgA Human TLR2 Detection and Neutralizing antibody—Monoclonal Human IgA2 (clone B4H2, catalog code maba2-htlr2); 2) Anti-mTLR2-IgG Mouse TLR2 Neutralizing antibody—Monoclonal Mouse IgG2a (clone C9A12; catalog code mabg-mtlr2); 3) MAb-hTLR2 Human TLR2 Detection antibody—Monoclonal Mouse IgG2a (TL2.1); 4) MAb-mTLR2 Mouse TLR2 Detection and Neutralizing antibody—Monoclonal Mouse IgG1 (clone T2.5; catalog code mab-mtlr2); and 5) PAb-hTLR2 Human TLR2 Neutralizing antibody—Polyclonal Rat IgG (catalog code pab-hstlr2).

Other useful antibodies directed against TLR2 include, but are not limited to, human TLR2 antibody mAb2616 (R&D Systems). Useful antibodies from Abcam include, but are not limited to, mouse monoclonal Anti-TLR2 antibody [TL2.1], product code ab9100, reactive against multiple species, including humans and is a neutralizing antibody; Anti-TLR2 antibody [EPNCIR133] product code ab108998, rabbit monoclonal with reactivity against multiple species, including humans; Anti-TLR2 antibody [T2.5], product code ab16894, mouse monoclonal cross reactive with multiple species, including humans; Anti-TLR2 antibody (product code ab213676), rabbit polyclonal cross reactive with multiple species, including humans; Anti-TLR2 antibody (product code ab191458), rabbit polyclonal cross reactive with multiple species, including humans; Anti-TLR2 antibody [T2.5] (FITC) (product code ab59711), mouse monoclonal cross reactive with multiple species, including humans; Anti-TLR2 antibody (product code ab1655), goat polyclonal directed against human TLR2; Anti-TLR2 antibody [TL2.1] (Biotin) (product code ab9101), mouse monoclonal directed against multiple species, including humans; Anti-TLR2 antibody [TL2.1] (FITC) (product code ab13553), mouse monoclonal against multiple species, including human; Anti-TLR2 antibody [TL2.1] (Phycoerythrin) (ab171568).

Useful antibodies from ThermoFisher include, but are not limited to neutralizing mouse CD282 (TLR2) monoclonal antibody (TL2.1) reactive with human, catalog no. 16-9922-82 or -83; and mouse IgG2a neutralizing TLR2 monoclonal antibody (TL2.1), catalog no. MA5-16200, cross-reactive with human. For purposes of neutralizing or inhibiting TLR2 activity, only antibodies with such properties will be used.

Clinical doses of antibodies are disclosed herein and are also known in the art. Doses can vary depending on the age, sex, weight, body surface area (BSA), and health of the subject. Additionally, a higher dose may be used in some cases where an immediate effect is needed. Doses can be administered as a unit dose or the dose can be based on criteria such as those describe above for body weight, etc. Cartron et al. (Blood, 2002, 99:754-758) used Rituximab in humans as a total of four 375 mg/m² doses by intravenous infusion spread out over several weeks. Maini et al. (Clinical Science, 1998, 41:9:1552-1563) used a monoclonal anti-tumor necrosis-factor α antibody (infliximab/Remicade) at 1, 3, or 10 mg/kg delivered intravenously in patients with rheumatoid arthritis and administered it at 0, 2, 6, 10 and 14 weeks. Single-dose administration of anti-interleukin-13 antibody (tralokinumab) at 300 mg in adolescents with asthma was well-tolerated (Baverel et al., Br. J. Clin. Pharmacol., 2015, 80:6:1337-1349). The anti-PDGFR antibody Imatinib has been used at varying doses in humans, including, for example, at daily doses of 400 mg, 600 mg and 800 mg (Michael et al., Cancer Chemother. Pharmacol., 2013, 71:2:321-330). Bebb et al. (Cancer Chemother. Pharmacol., 2011, 67:4:837-845) used the anti-EGFR monoclonal antibody nimotuzumab in humans at doses of 100 mg, 200 mg and 400 mg weekly and stated that it has been shown to be well tolerated at doses of 50-800 mg. The T2.5 monoclonal antibody that is antagonistic to TLR2 has been used to prevent lethal shock-like syndrome and it increased survival with administered 1 hour before or up to 3 hours after infection (Meng et al, J. Clin. Invest., 2004, 113:1473). It was effective at 40 mg/kg for this short-term treatment used for preventing or treating shock-like syndrome at the time of infection and pre-treatment with 0.5 mg or 1.0 mg were effective. Intracellular antibodies have also been used to block translocation of TLR2. Spiller et al. (J. Exp. Med., 2008, 205:8:1747-1754) used an anti-TLR2 antibody (T2.5) at 30 mg/kg to prevent or treat sepsis after LPS injection.

In one embodiment, a therapeutic dose of an antibody of the invention, including, but not limited to, monoclonal antibodies, chimeric antibodies, humanized antibodies, various kinds of fragments, and biologically active homologs and fragments thereof, is from about 0.1 mg/dose to about 5,000 mg/dose or from about 0.2 mg/dose to about 1,000 mg/dose. Doses can also be administered based on body weight, for example at a dosage ranging from about 0.01 mg/kg to about 1,000 mg/kg body weight or from about 0.1 to about 500 mg/kg.

In accordance with the present invention, as described above or as discussed in the Examples below, there can be employed conventional chemical, cellular, histochemical, biochemical, molecular biology, microbiology, clinical, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention. The following working examples therefore, are provided for the purpose of illustration only and specifically point out the embodiments of the present invention, and are not to be construed as limiting in any way the remainder of the disclosure. Therefore, the examples should be construed to encompass any and all variations which become evident as a result of the teaching provided herein.

Other useful techniques that can be practiced with the present invention can be found in the art.

EXAMPLES

Summary—A series of experiments disclose that IL-33 promotes a protective host immune response during hypervirulent *C. difficile* infection. Interleukin-33 (IL-33) is a member of the IL-1 family of cytokines and functions both as an alarmin, released from cells upon death, and as a cytokine capable of inducing type-2 immunity (17). After release, IL-33 binds to its primary receptor, ST2, that is expressed on a variety of innate and adaptive cells including macrophages, dendritic cells, group 2 innate-lymphoid cells, eosinophils, regulatory T cells, and T helper 2 cells (18).

The data demonstrate that CDT toxin increases virulence via a TLR2 dependent mechanism. Furthermore, treatment with recombinant interleukin-33 (IL-33), a protein upregulated in guts of protected TLR2−/− mice, protects from associated mortality and weight-loss.

Materials and Methods

Mice and *Clostridium difficile* Infection

Experiments were carried out using sex matched 8-12 week old C57BL6 and TLR2−/− mice purchased from Jackson Laboratory. All animals were housed under specific pathogen free conditions at the University of Virginia's animal facility and procedures were approved by the Institutional Animal Care and Use Committee at the University of Virginia (IACUC). Bedding exchange every two days between TLR2−/− and C57BL6 mice for a minimum of two weeks was conducted to equilibrate microbiota between strains. Mice were infected using a previously published murine model for CDI[10,21,22]. Three days prior to infection, mice were given an antibiotic cocktail in drinking water consisting of 45 mg/L Vancomycin (Mylan), 35 mg/L Colistin (Sigma), 35 mg/L Gentamicin (Sigma), 215 mg/L Metronidazole (Hospira). This antibiotic cocktail was used in other experiments as well. Mice were then switched to regular drinking water and given a single IP injection (0.032 mg/g) of Clindamycin (Hospira) on Day −1. On Day 0, mice were orally gavaged with $1 \times 10^6$ CFU/ml of *C. difficile*. For IL-33 treatment, mice were intraperitoneally injected for 5 days prior to infection with 0.75 μg in 100 μl of carrier-free, recombinant mouse IL-33 (Biolegend; Catalog #: 580504—Mouse IL-33; a peptide comprising amino acid residues Ser109-Ile266 of the 266 amino acid protein (Accession # AAH03847.1) was expressed in *E. coli*. The 158 amino acid recombinant protein has a predicted molecular mass of approximately 17,554 Da. The DTT-reduced and non-reduced protein migrate at approximately 20 kDa by SDS-PAGE. The N-terminal amino acid is Serine). The Biolegend recombinant protein is listed as SEQ ID NO:12 herein and the 266 amino acid protein is listed as SEQ ID NO:11 herein.

Mice were monitored twice daily over the course of infection and evaluated according to clinical scoring parameters. Scores were based on weight loss, coat condition, activity level, diarrhea, posture, and eye condition for a cumulative clinical score between 1 and 20. Mice were euthanized if severe illness developed based on a clinical score ≥14.

Bacterial Strains and Culture

Isogenic *C. difficile* strain R20291 CdtB—was generated using the ClosTron system of insertional mutagenesis and inactivation CDTb was confirmed by Western blot[23]. To prepare the *C. difficile* inoculum, strains were plated onto BHI agar from frozen stocks and incubated at 37° C. overnight in an anaerobic work station (Shel Labs). A single colony was inoculated into BHI medium and grown anaerobically overnight at 37° C. The next day, cultures were spun for 1 minute at 6,000×g and washed twice in anaerobic PBS and the optical density was measured. The culture density was adjusted in anaerobic PBS to $1 \times 10^8$ CFU/mL and loaded into syringes. Each mouse received 100 μl ($1 \times 10^7$ CFU) of inoculum by oral gavage. *C. difficile* burden was quantified from cecal contents at Day 2 of infection. Briefly, cecal contents were resuspended by weight in anaerobic PBS. Serial dilutions of cecal contents were plated on BHI Agar supplemented with 1% Sodium Taurocholate, 1 mg/mL D-cycloserine and 0.032 mg/mL cefoxitin (Sigma) and anaerobically incubated at 37° C. overnight followed by colony counts in triplicate.

IL-33 Tissue Protein

IL-33 was detected in cecal tissue lysates using the Mouse IL-33 Duoset Sandwich ELISA (R & D) according to manufacturer's instructions. Total cecal lysate was generated by removing the ceca and rinsing gently with 1×PBS. Tissue was bead beaten for 1 minute resuspended in 400 ul of Lysis Buffer I: 1×HALT Protease Inhibitor (Pierce), 5 mM HEPES. Following mechanical tissue disruption, 400 ul of Lysis Buffer II was added: 1×HALT Protease Inhibitor (Pierce), 5 mM HEPES, 2% Triton X-100. Tissue samples were incubated on ice for 30 minutes after gently mixing. Lysed samples were pelleted to remove tissue debris in a 5 minute spin at 13,000×g at 4° C. Supernatant was collected and total protein concentration was measured by BCA assay according to manufacturer's instructions (Pierce). IL-33 cytokine concentration was normalized to total protein concentration.

Flow Cytometry

Colons were dissected longitudinally and rinsed in HBSS supplemented with 25 mM HEPES and 5% FBS. Epithelial cells were separated from the lamina propria via a 40 min incubation with gentle agitation in dissociation buffer (HBSS with 15 mM HEPES, 5 mM EDTA, 10% FBS and 1 mM DTT) at 37° C. Next, the lamina propria tissue was manually diced using scissors and further digested in RPMI 1640 containing 0.17 mg/mL Liberase TL (Roche) and 30 μg/mL DNase (Sigma). Samples were digested for 40 minutes at 37° C. with gentle shaking. Single cell suspensions were generated by passaging samples through a 100 μM cell strainer followed by a 40 uM cell strainer (both Fisher Scientific). $1 \times 10^6$ cells/sample were Fc-blocked with TruStain fcX (anti-mouse CD16/32 antibody, BioLegend) for ten minutes at room temperature followed by LIVE/DEAD Fixable Aqua (Life Technologies) for 30 minutes at 4° C. Cells were washed twice in FACS buffer (PBS+2% FBS) and stained with fluorochrome conjugated antibodies for 30 minutes at 4° C. Cells were washed and resuspended in Foxp3 Fix/Perm Working Solution (Ebiosciences) and incubated overnight at 4° C. Cells were washed twice with Permeabilization buffer and stained for nuclear Foxp3-APC (Ebioscience) for 30 minutes at room temperature. Cells were washed twice and resuspended in FACs buffer. Flow cytometry was performed on an LSR Fortessa cytometer (BD Biosciences) and all data analysis performed via FlowJo (Tree Star Inc.).

IL-33 Proteins and Fragments

Various precursor, fragment, and variants of IL-33 can be prepared or are available in purified form from other sources. For example, Novoprotein's recombinant IL-33, catalog # C091 (Uniprot Accession No. 095760; see SEQ ID NO:8) is a recombinant human IL-33 produced by their *E. coli* expression system and the target gene encoding Ser112-Thr270 (160 residues) is expressed. Human IL-33 is also available from Origene (Cat. No. TP723227 (tag-free; see SEQ ID NO:9). See also SEQ ID NOs:1-12.

Results

Figure 3:
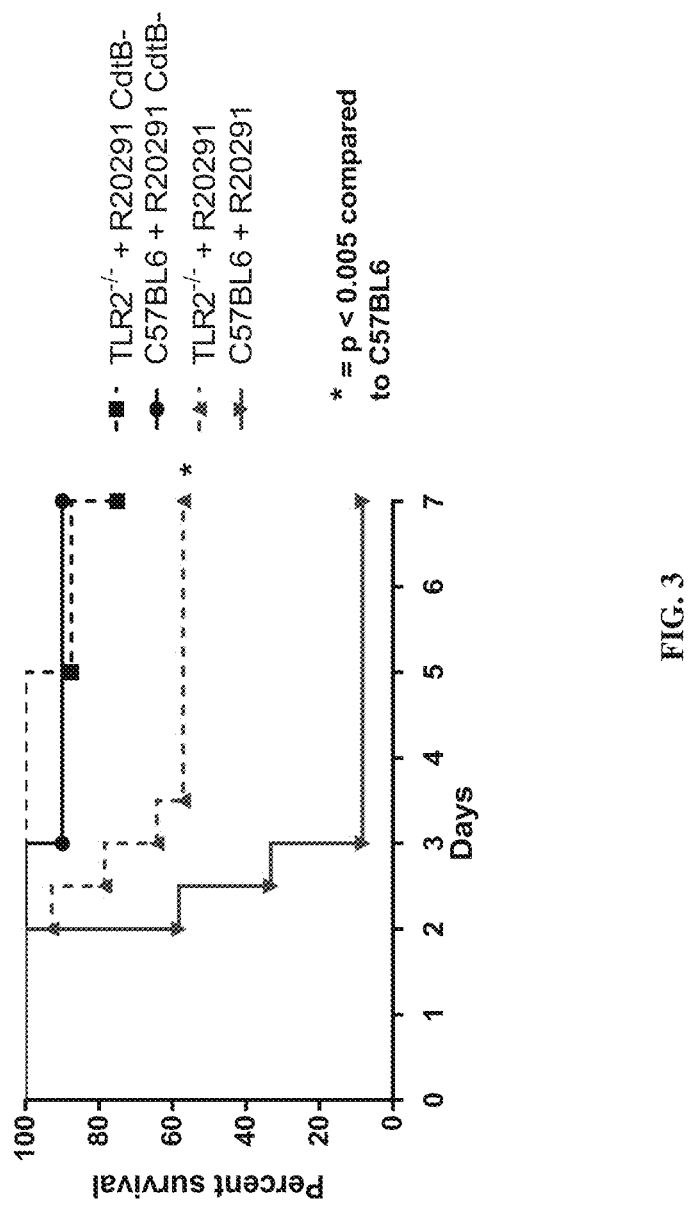
FIG. 3. TLR2 IS PATHOGENIC TO THE HOST DURING CDI—TLR2−/− mice are significantly protected from CDT associated mortality—reproduced from Cowardin & Petri et al. *Nature Micr.*, 2016. Mice lacking TLR2 (TLR2−/−) are significantly protected from CDT expressing *C. difficile* (strain R20291) associated mortality. TLR2−/− and wildtype mice were cohoused for 3 weeks prior to infection. Wildtype and TLR2−/− mice were treated for 3 days with an antibiotic cocktail to disrupt their microbiota. After antibiotic treatment, mice were infected with $1 \times 10^7$ CFU of R20291.

To characterize how TLR2−/− mice are protected from NAPI/027 pathogenesis, we conducted a microarray of cecal tissue isolated from either protected TLR2−/− mice or susceptible wildtype mice, infected with a CDT-expressing NAPI/027 strain (R20291) or an isogenic mutant strain lacking functional CDT expression (R20291 CDT−). Through this microarray, we found a significant negative enrichment for IFN-y responses (FIG. 3A), inflammatory responses (FIG. 3B) and TNF-α signaling via NF-kB (FIG. 3C) in TLR2−/− mice in response to CDT+C. *difficile* infection. Additionally, there was a significant downregulation in IL-1β and IL-1α transcripts in protected TLR2−/− mice compared to susceptible wildtype mice.

These data indicate there is a lack of inflammatory pathway upregulation in protected TLR2−/− mice as seen in susceptible wildtype mice. These data are in alignment with our previous study demonstrating that TLR2 recognizes CDT toxin and induces NF-kB activation and pro-IL-1β expression[10].

Role of IL-33

Figure 4A:
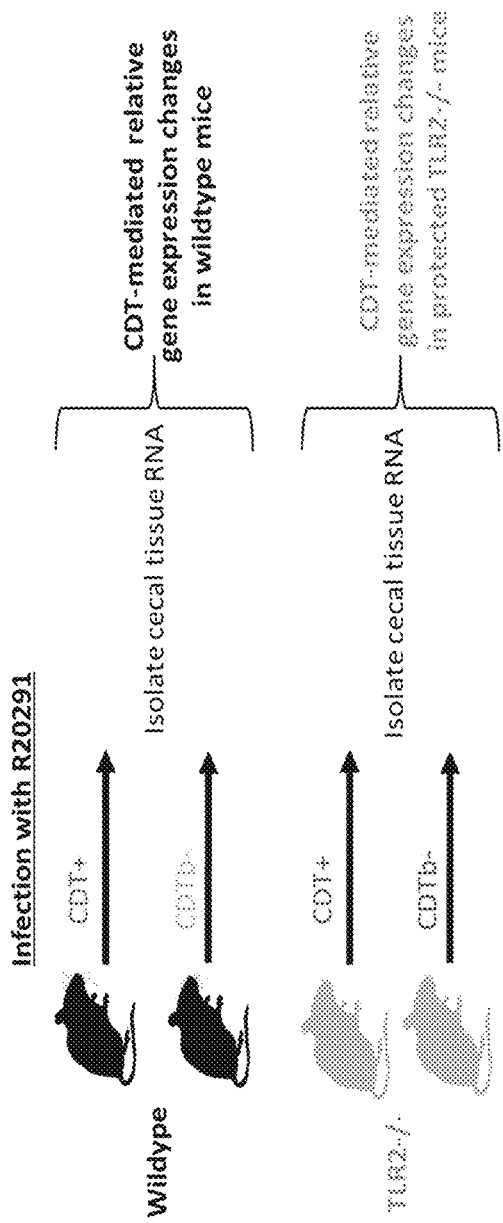
FIG. 4A. Experimental Design for Affymetrix Microarray.
Figure 4B:
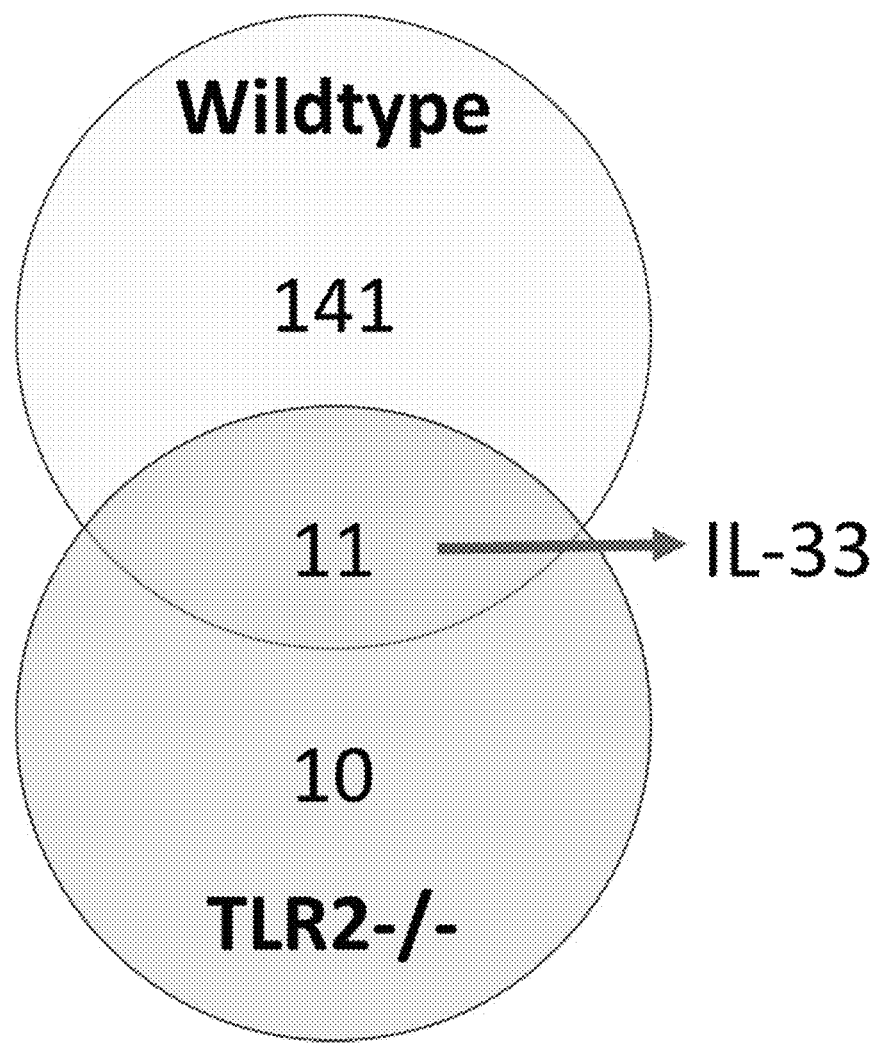
FIG. 4B. Venn diagram of genes upregulated by CDT toxin.
Figure 4C:
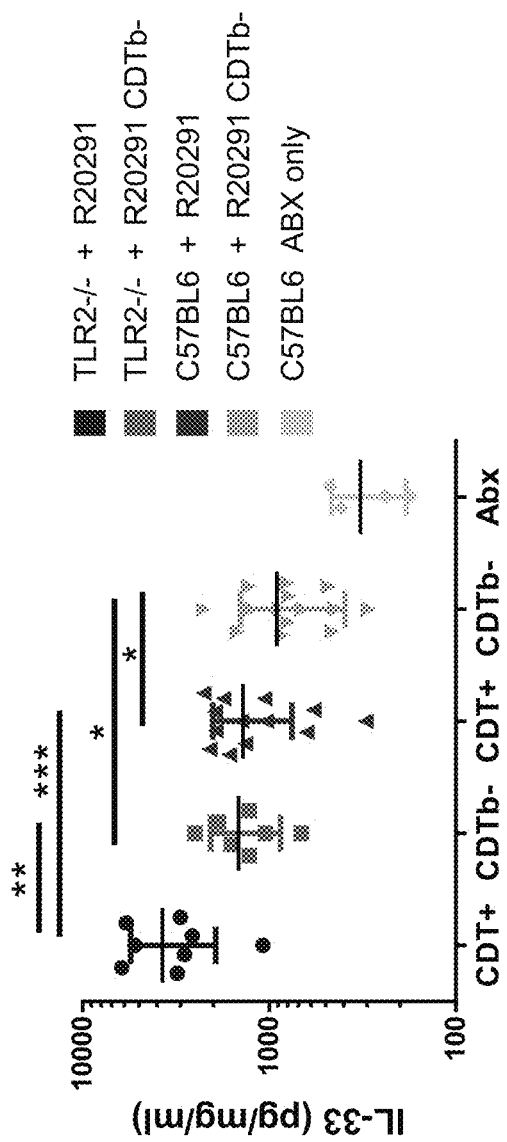
FIG. 4C. IL-33 protein in infected cecal tissue. IL-33 protein, identified via microarray, is significantly increased in protected TLR2−/− mice compared to wildtype mice during CDT+ or CDT− *C. difficile* infection.

Through this microarray, we now identify IL-33 as a gene significantly upregulated by CDT toxin in the colon of protected TLR2−/− mice. It can be seen that IL-33 protein was increased within the colon of protected TLR2−/− mice infected with *C. difficile* (both CDT+ and CDTb− R20291 strains) (see FIG. 4A-C). These data led us to hypothesize that IL-33 is a protective immune cytokine in the gut during *C. difficile* infection.

Figure 11:
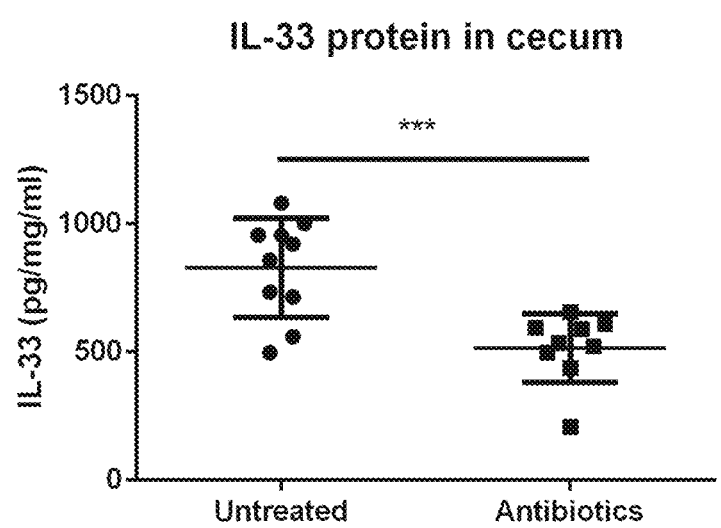
FIG. 11. PROTECTIVE IL-33 IS DEPLETED IN THE GUT BY ANTIBIOTIC THERAPY. IL-33 protein in mouse cecal tissue measured by ELISA. The untreated vs antibiotics IL-33 was compared using a student t test. *P<0.001; P<0.01; *P<0.05.

Further experiments were performed to determine the effects of antibiotic treatment on IL-33 in the gut. IL-33 protein was measured by ELISA in mouse cecal from animals treated with antibiotics or control (untreated) animals. It was found that IL-33 is depleted in the colon during antibiotic therapy of mice, indicating that IL-33 levels may be regulated by the microbiota and antibiotic therapy (see FIG. 11). Antibiotics are the biggest risk factor for acquiring *C. difficile* infection, therefore, replenishing protective IL-33 in the gut while a patient is on antibiotics could be very important. Furthermore, using probiotics to replenish IL-33 may be an additional mode to increase IL-33 in the gut.

Figure 5A:
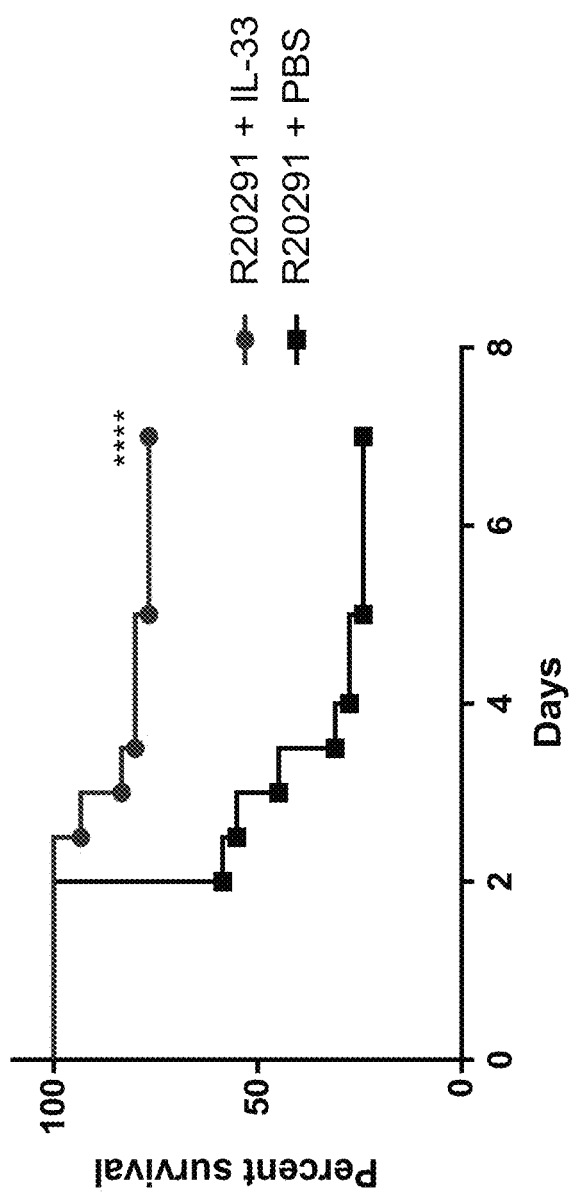
FIG. 5A. Survival.
Figure 5B:
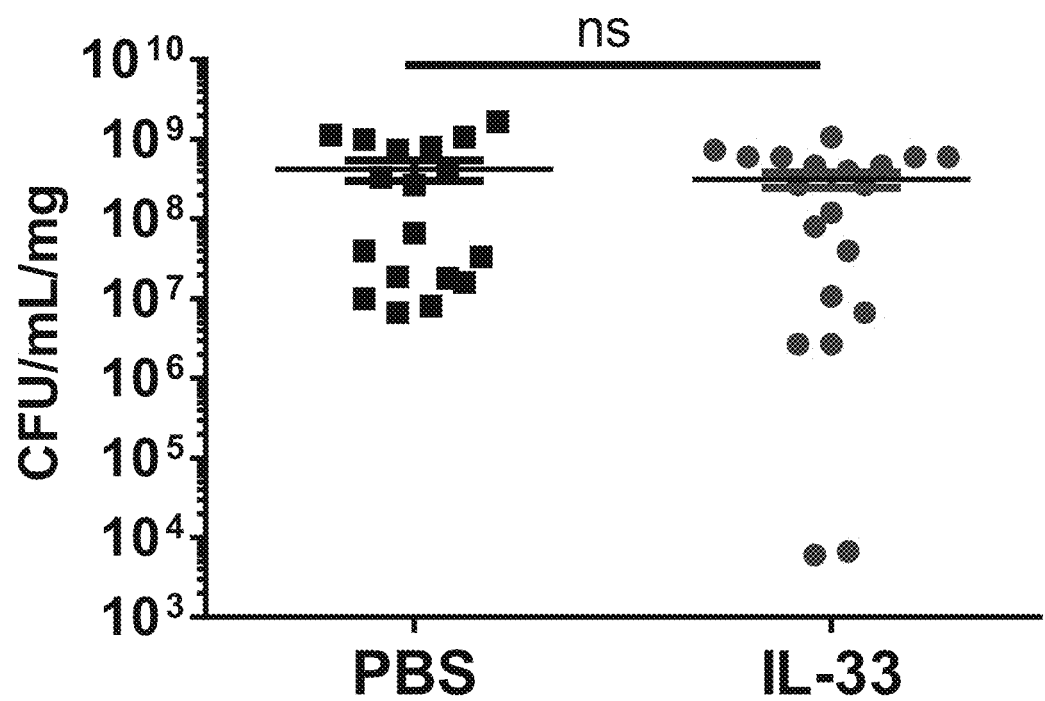
FIG. 5B. *C. difficile* burden. 8-week old C57B1/6J mice were treated with antibiotics and infected with $1 \times 10^7$ CFU of *C. difficile* epidemic strain R20291. Mice were IP injected with 0.75 μg of IL-33 (in 100 μl) or PBS on days −4, −3, −2, −1, and 0 of infection. Survival curves compared using a log-rank statistical test. The IL-33 vs PBS bacterial burden was compared using a student t test. Data represents 2 combined experiments (10 mice per group per experiment) **P<0.0001; *P<0.001; **P<0.01; *P<0.05; ns=not significant.
Figure 9:
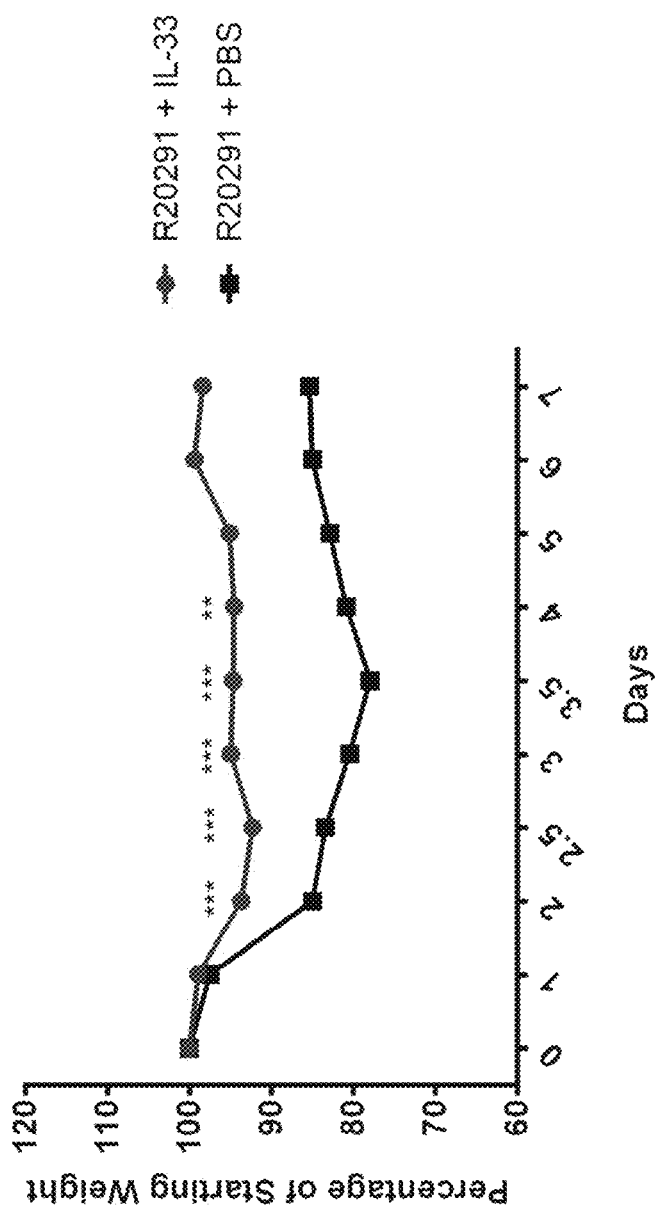
FIG. 9: RECOMBINANT IL-33 PROTECTS AGAINST CDT MEDIATED VIRULENCE AND WEIGHT LOSS. Mice administered 0.5 μg recombinant IL-33 are protected from hypervirulent, CDT expressing R20291 *C. difficile* epidemic isolate, including protection from weight loss. The ordinate represents Percentage of Starting Weight and the abscissa represents the day from initiation of treatment. One group was treated with IL-33 and the other with PBS. 8-week old C57B1/6J mice were treated with antibiotics and infected with $1 \times 10^7$ CFU of *C. difficile* epidemic strain R20291. Mice were IP injected with 0.75 μg of IL-33 (in 100 μl) or PBS on days −4, −3, −2, −1, and 0 of infection. Survival curves compared using a log-rank statistical test. The IL-33 vs PBS weight loss was compared using a student t test. Data represents 2 combined experiments (10 mice per group per experiment) **P<0.0001; *P<0.001; **P<0.01; *P<0.05.

To specifically assess the role of IL-33 during NAPI/027 infection, we treated mice with recombinant IL-33 (rIL-33) or PBS for 5 days. Strikingly, mice treated with rIL-33 were significantly protected from NAPI/027-associated mortality (FIG. 5A). Interestingly, IL-33 protection was not caused by decreased *C. difficile* bacterial burden (FIG. 5B) and it also protected against weight loss (FIG. 9).

Figure 6A:
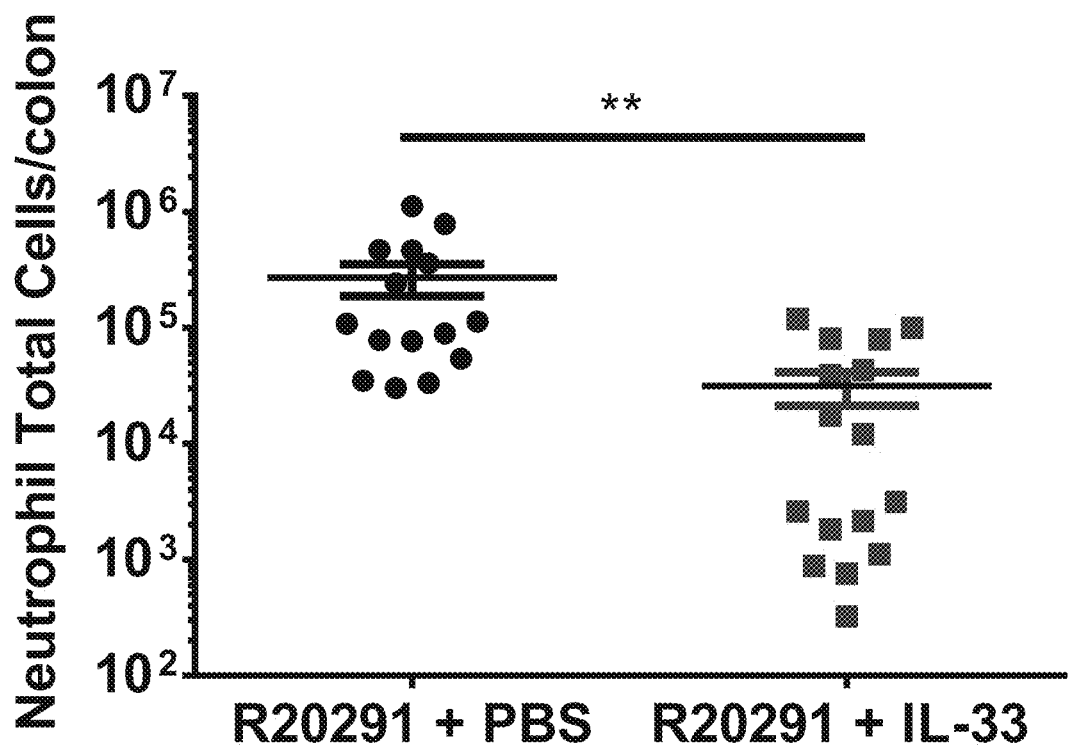
FIG. 6A. Ly6C+ Ly6G+ Neutrophil number.
Figure 6B:
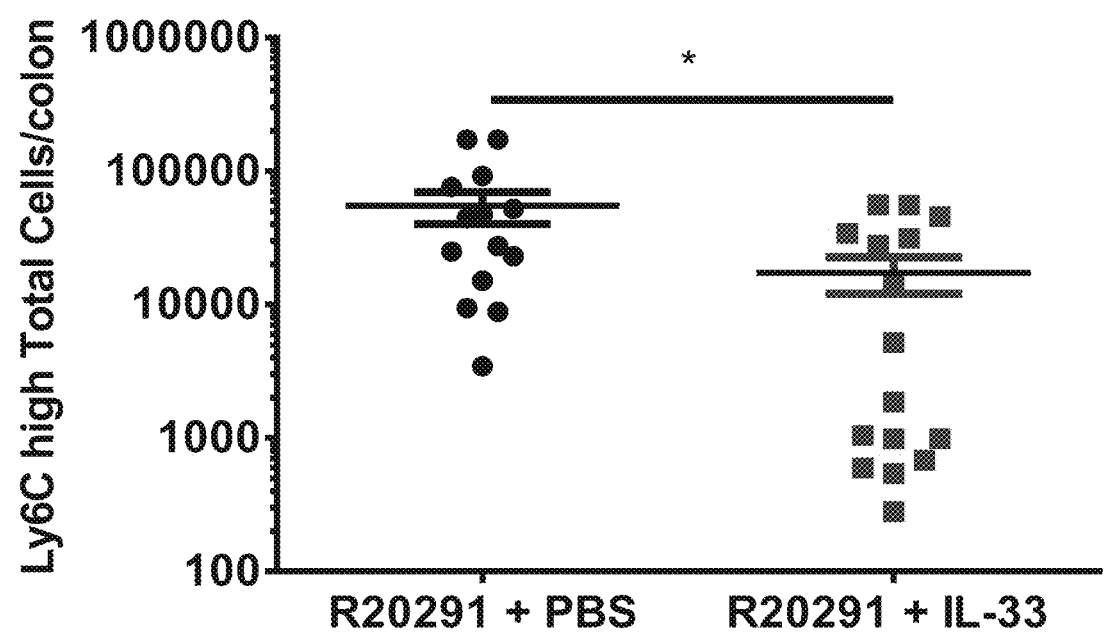
FIG. 6B. Ly6C High Monocytes number.
Figure 6C:
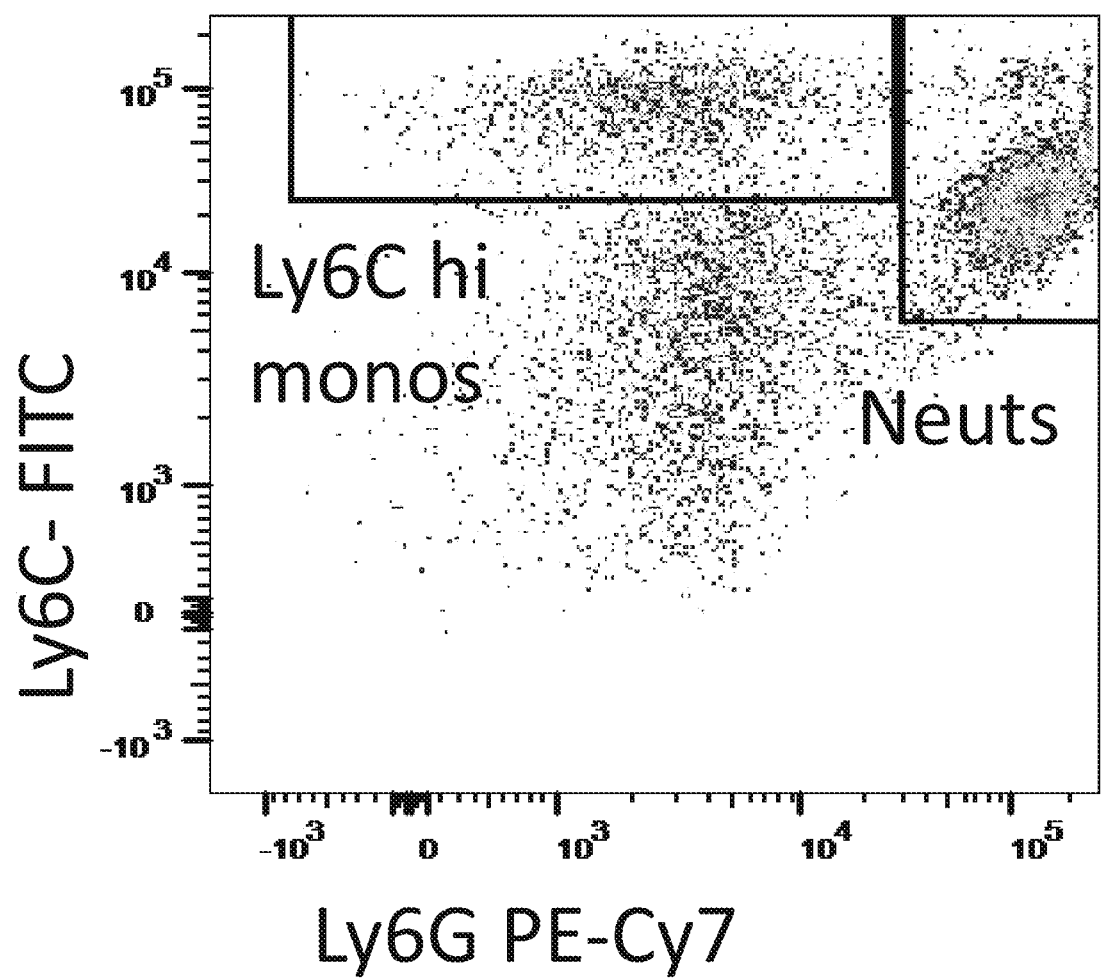
FIG. 6C. PBS Treated.
Figure 6D:
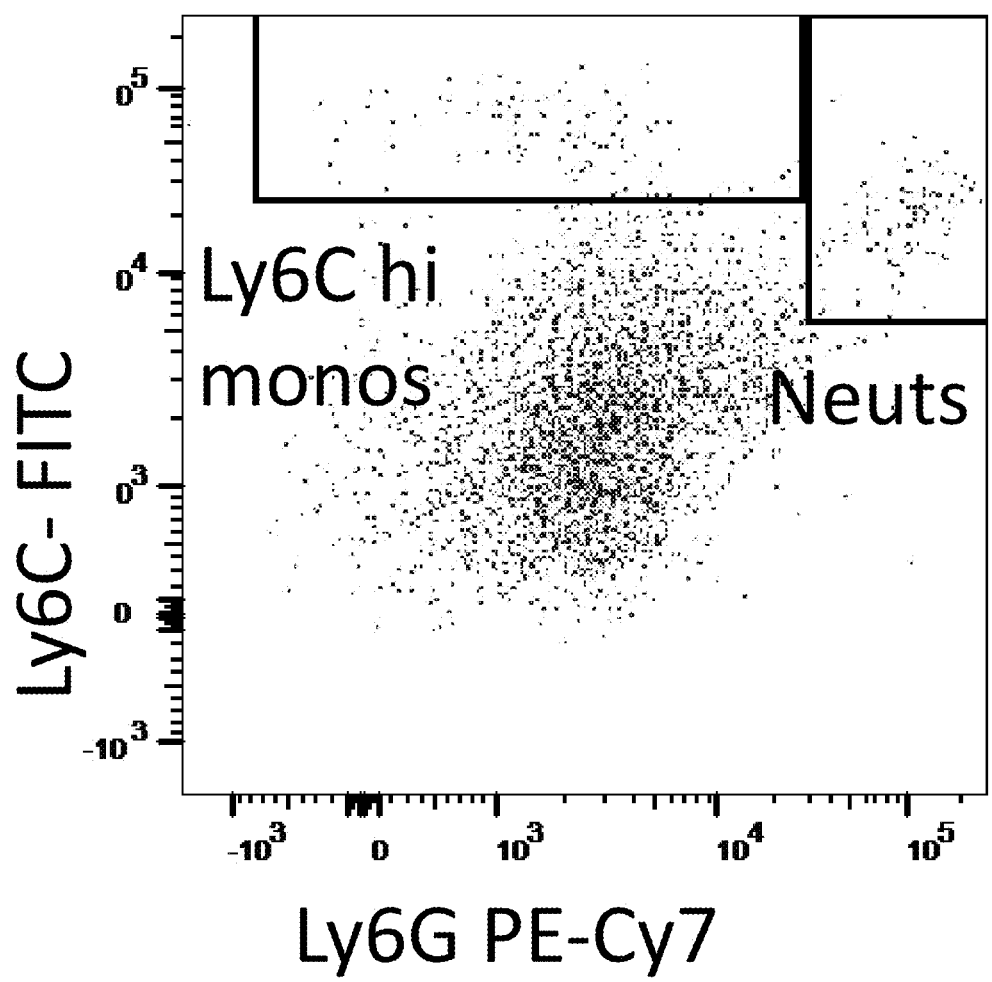
FIG. 6D. IL-33 Treated. Total neutrophil number (FIG. 6A) and frequency (FIG. 6B) and total $Ly6c^{high}$ monocyte number (FIG. 6C) and frequency of live (FIG. 6D) in the colon of IL-33 treated or PBS treated C57BL6 mice on Day 2 of R20291 *C. difficile* infection. Student t test ** p<0.0001 * p<0.001 **p<0.01 * p<0.05.

When characterizing the cellular immune response in the colon during *C. difficile* infection, IL-33-treated mice had significantly reduced neutrophilic (FIGS. 6A and 6B) and inflammatory monocyte (FIGS. 6C and 6D) infiltration compared to PBS controls.

Figure 7A:
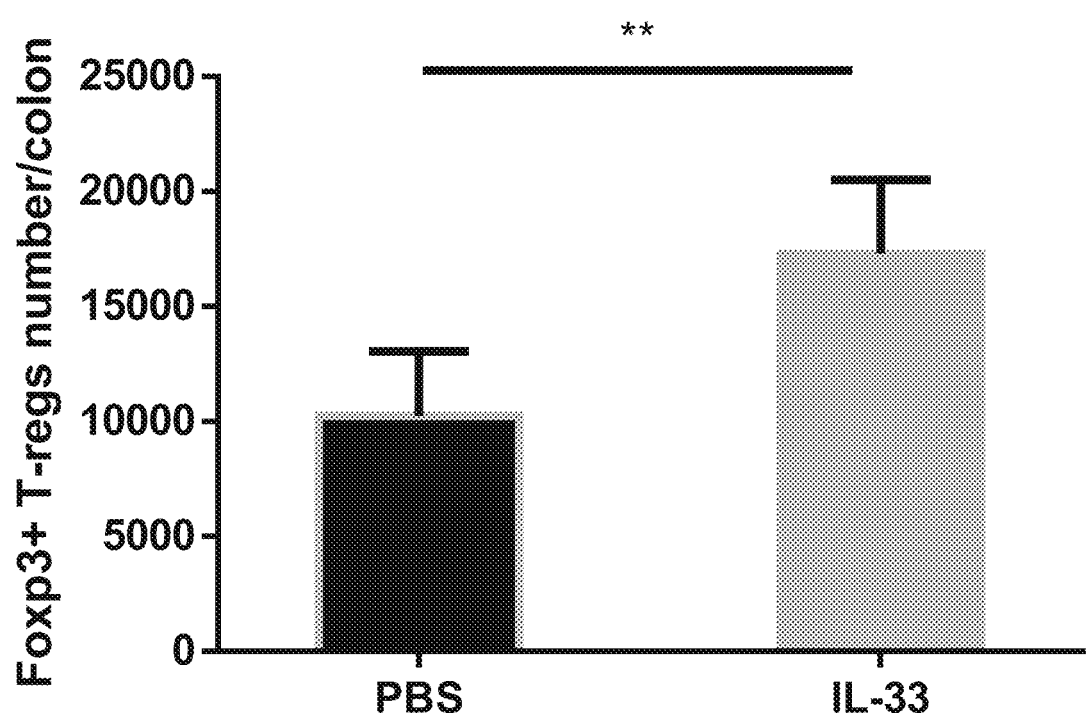
FIG. 7A. Foxp3+ CD4+ colonic T-regs.
Figure 7B:
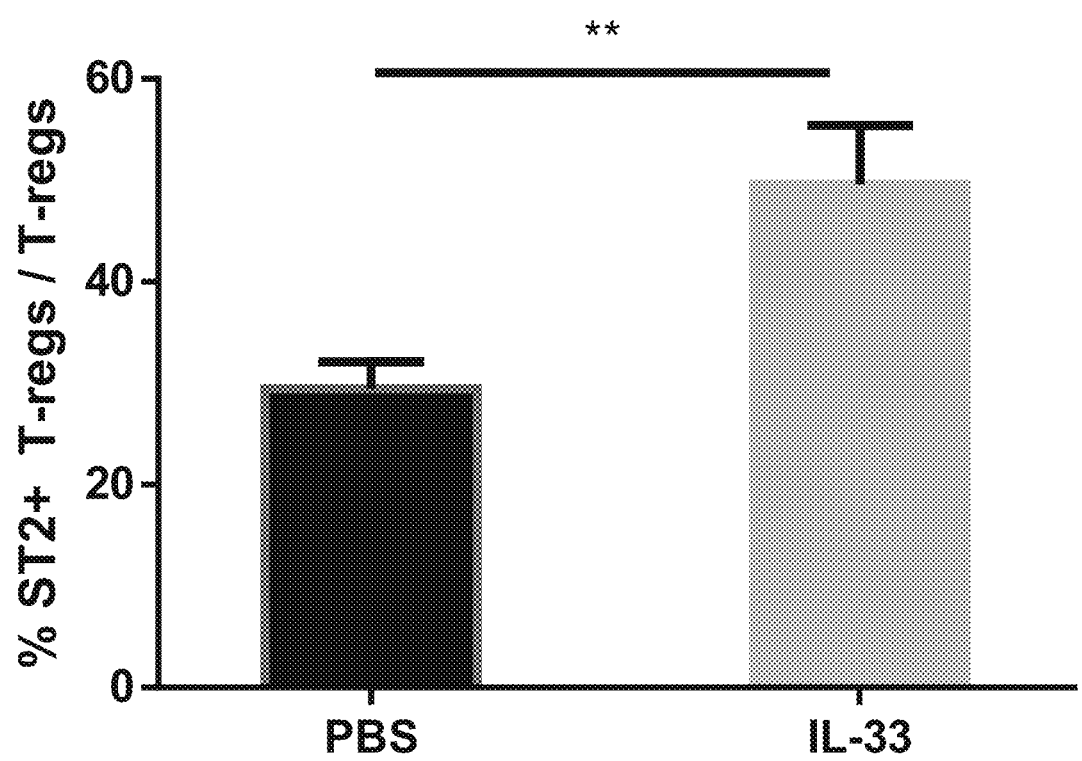
FIG. 7B. % ST2+ colonic T-regs.
Figure 7C:
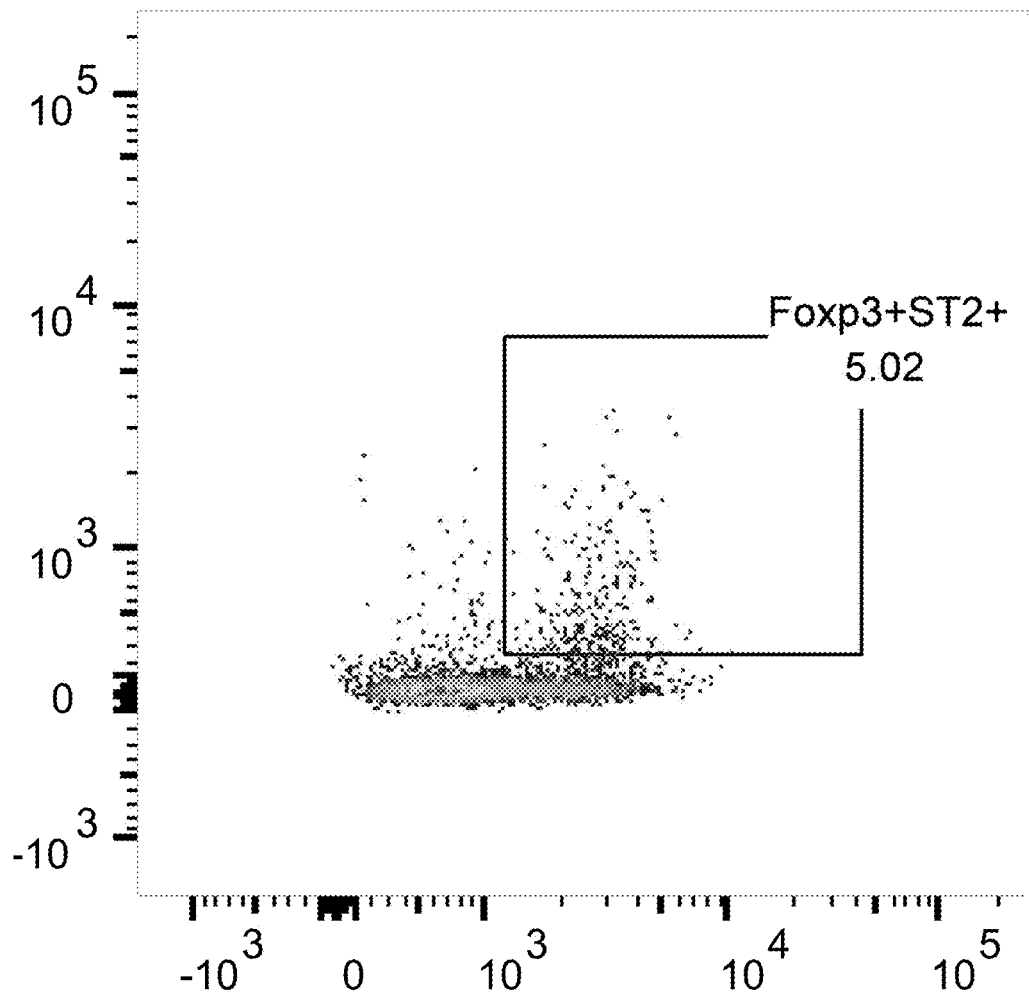
FIG. 7C. PBS Treated.
Figure 7D:
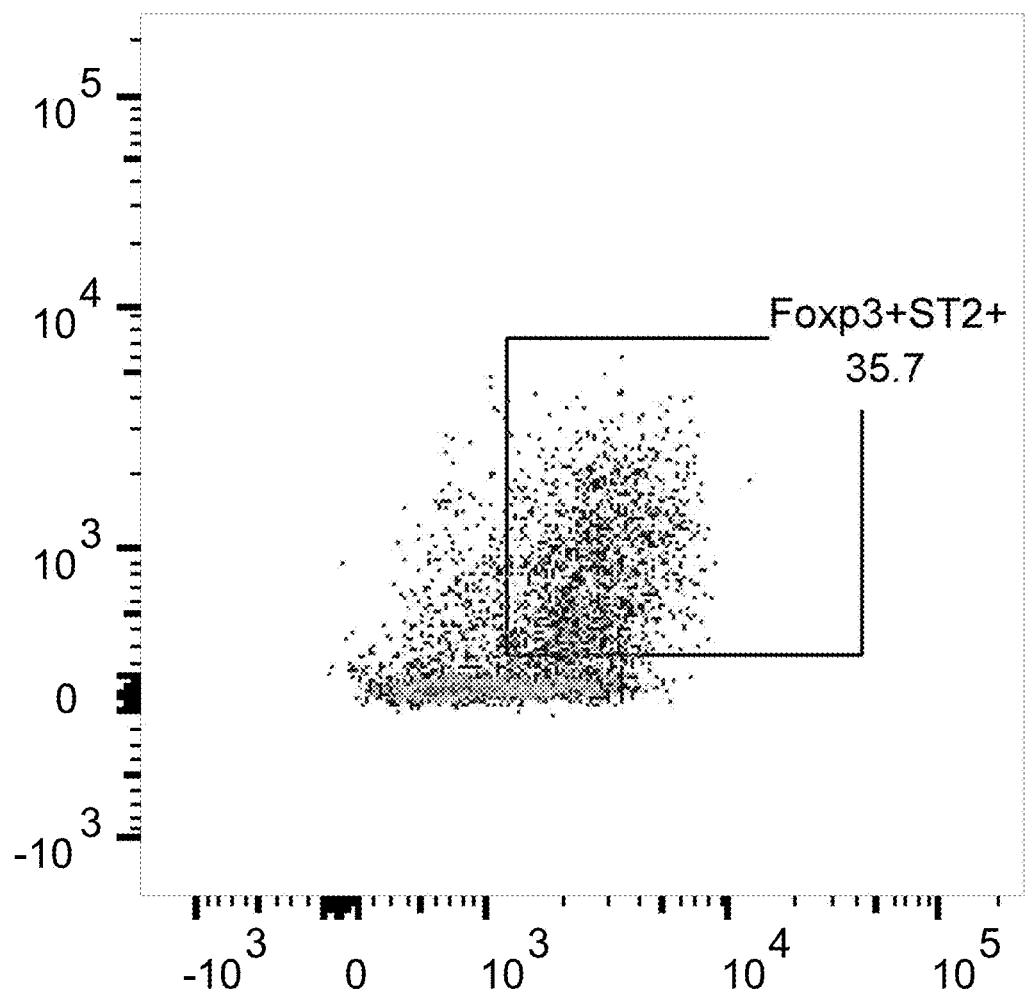
FIG. 7D. IL-33 Treated.
Figure 8:
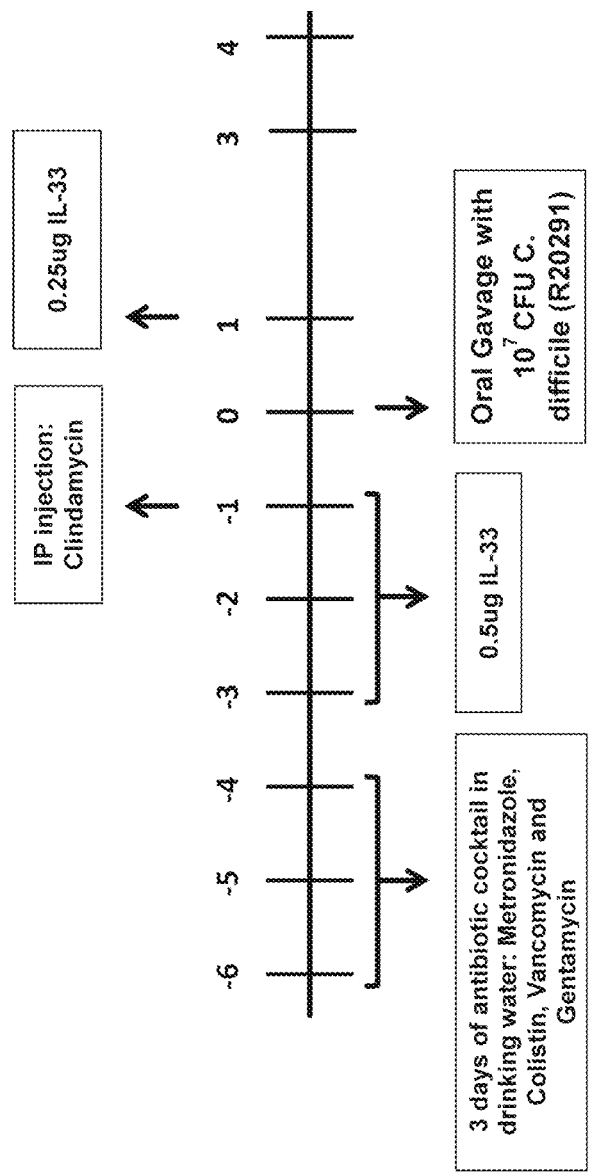
FIG. 8: IL-33 INTERVENTION EXPERIMENTAL DESIGN SCHEMATIC. Mice are pre-treated on days −6 to −3 with 3 days of an antibiotic cocktail in drinking water (metronidazole, colistin, vancomycin, and gentamicin). IL-33 (0.5 μg) is administered intraperitoneally on days −3, −2, −1 and 1. After a final antibiotic treatment (clindamycin) on day −1, mice receive an oral challenge with $10^7$ CFU *C. difficile* (R20291).
Figure 10:
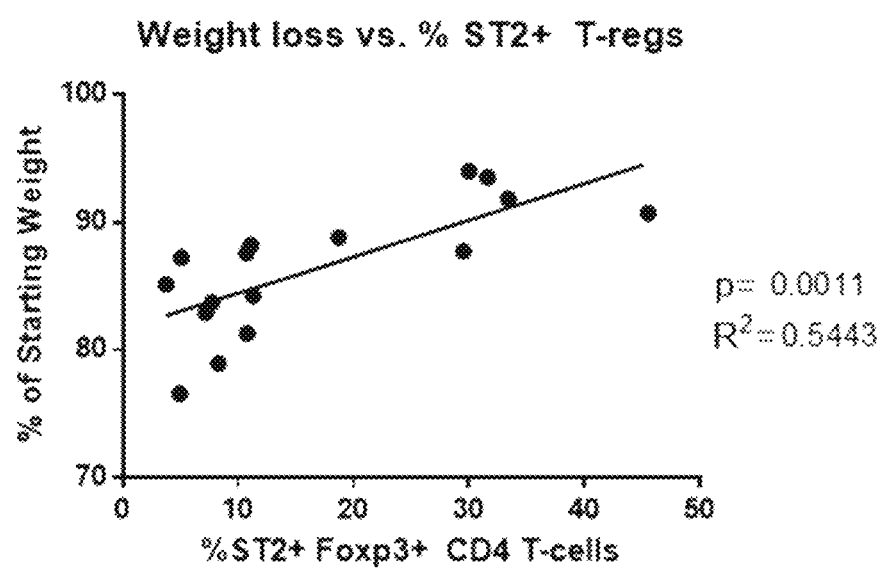
FIG. 10. PROTECTIVE ROLE FOR ST2+ CELLS AND CORRELATION WITH LESS WEIGHT LOSS. Percentage of live of ST2+ Foxp3+ regulatory T cells in the colon of PBS and IL-33-treated mice plotted against weight-loss on day 3 of *C. difficile* infection.

Additionally, IL-33 treated mice have an increase in Foxp3+ regulatory CD4+ T cells in their colon during *C. difficile* infection (FIG. 7A). Furthermore, regulatory CD4+ T cells in IL-33 treated mice upregulated the expression of the IL-33 receptor (ST2) (FIG. 7B). Regulatory T cells expressing ST2 are highly activated and are protective in models of ulcerative colitis[17,19,20] supporting a potential protective role for ST2+ regulatory T cells in the colon during *C. difficile* infection in our model. Consistent with this idea, we see a significant correlation between the frequency of ST2+ Foxp3+ regulatory T cells and less weight-loss during *C. difficile* infection (FIG. 10).

See FIGS. 1-11.

Summary and Conclusion

Hypervirulent epidemic strains of *C. difficile* are increasing in prevalence within US health-care facilities. These strains are associated with higher mortality and relapse rates and express a new, third toxin called binary toxin (CDT). CDT increases disease severity and mortality by activation of the toll-like receptor 2 (TLR2) pathway. Through a microarray of global gene expression changes in the colon, we identified IL-33 as a candidate immune gene increased in protected TLR2−/− mice. Our data show that IL-33 treatment protects from *C. difficile* associated mortality, weight-loss and induces tissue protective ST2+ regulatory T cells during infection. The frequency of colonic ST2+ regulatory T cells correlates with less weight-loss indicating these cells may be the source of IL-33 protection from CDI-associated mortality. We are continuing further studies to understand the necessity and functional role of ST2+ regulatory T cells during *C. difficile* infection.

1. CDT toxin increases the virulence of epidemic *C. difficile*.
2. TLR2−/− mice are protected from CDT associated mortality and have increased colonic IL-33 protein relative to wildtype mice.
3. Antibiotic treatment reduces colonic IL-33.
4. IL-33 treatment protects from R20291 (CDT+) virulence independent of *C. difficile* burden.
5. IL-33 treatment is anti-inflammatory; decreasing neutrophil and Ly6c[hi] monocyte inflammation.
6. IL-33 treatment expands colonic Foxp3+ ST2+ regulatory T-cells during *C. difficile* infection.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Kelly, C. P. & LaMont, J. T. *Clostridium difficile*—more difficult than ever. N. Engl. J. Med. 359, 1932-1940 (2008).
2. The White House Administration. National Action Plan for Combating Antibiotic-Resistant Bacteria. Open Government National Action Plans (2015).
3. Infectious National Institute of Allergy and Diseases. NIAID â€TM s Antibacterial Resistance Program: Current Status and Future Directions. (2014).
4. National Institute of Allergy and Infectious Diseases. NIAID Emerging Infectious Diseases/Pathogens. National Institute of Health 1-5 (2015). Available at: https://www.niaid.nih.gov/topics/biodefenserelated/biodefense/pages/cata.aspx.
5. Aslam, S., Hamill, R. J. & Musher, D. M. Treatment of *Clostridium difficile*-associated disease: old therapies and new strategies. Lancet Infect. Dis. 5,549-57 (2005).
6. Bartlett, J. G. Annals of Internal Medicine Review Narrative Review: The New Epidemic of *Clostridium difficile*-. An. Intern. Med. 758-764 (2006).
7. Rupnik, M., Wilcox, M. H. & Gerding, D. N. *Clostridium difficile* infection: new developments in epidemiology and pathogenesis. Nat. Rev. Microbiol. 7, 526-36 (2009).
8. Gerding, D. N., Johnson, S., Rupnik, M. & Aktories, K. *Clostridium difficile* binary toxin CDT: mechanism, epidemiology, and potential clinical importance. Gut microbes 5, 15-27 (2014).
9. Papatheodorou, P. et al. Lipolysis-stimulated lipoprotein receptor (LSR) is the host receptor for the binary toxin *Clostridium difficile* transferase (CDT). Proc. Natl. Acad. Sci. U.S.A. 108, 16422-7 (2011).

10. Carrie A. Cowardin, Erica L. Buonomo, Mahmoud M. Saleh, Madeline G. Wilson, Stacey L. Burgess, Sarah A. Kuehne, Carsten Schwan, Anna M. Eichhoff, Friedrich Koch-Nolte, Dena Lyras, Klaus Aktories, Nigel P. Minton, William A. Petri, J. The binary toxin CDT enhances *Clostridium difficile* virulence by suppressing protective colonic eosinophilia. Nat. Microbiol. 1, 1-10 (2016) (1(8): 16108, doi:10.1038/nmicrobiol.2016.108., Published online: Jul. 11, 2016).
11. Akira, S. & Takeda, K. Toll-like receptor signalling. Nat. Rev. Immunol. 4, 499-511 (2004).
12. Cowardin, C. A. et al Inflammasome activation contributes to interleukin-23 production in response to *Clostridium difficile*. MBio 6, 1-9 (2015).
13. Andrews, K., Abdelsamed, H., Yi, A. K., Miller, M. A. & Fitzpatrick, E. A. TLR2 Regulates Neutrophil Recruitment and Cytokine Production with Minor Contributions from TLR9 during Hypersensitivity Pneumonitis. PLoS One 8, (2013).
14. Lin, H. Y. et al. Peptidoglycan induces interlukin-6 expression through the TLR2 receptor, JNK, c-Jun, and AP-1 pathways in microglia. J. Cell. Physiol. 226, 1573-1582 (2011).
15. Lin, H. Y. et al. Peptidoglycan enhances proinflammatory cytokine expression through the TLR2 receptor, MyD88, phosphatidylinositol 3-kinase/AKT and NF-kappaB pathways in BV-2 microglia. Int. Immunopharmacol. 10, 883-891 (2010).
16. Cantó, E. et al. TNFα production to TLR2 ligands in active IBD patients. Clin. Immunol. 119, 156-165 (2006).
17. Haraldsen, G., Balogh, J., Pollheimer, J., Sponheim, J. & Küchler, A. M. Interleukin-33—cytokine of dual function or novel alarmin? Trends in Immunology 30, 227-233 (2009).
18. Schmitz, J. et al. IL-33, an interleukin-1-like cytokine that signals via the IL-1 receptor-related protein ST2 and induces T helper type 2-associated cytokines. Immunity 23, 479-490 (2005).
19. Schiering, C. et al. The alarmin IL-33 promotes regulatory T-cell function in the intestine. Nature 513, 564-8 (2014).
20. Liu, Q. et al. IL-33-Driven Innate Tissue-Protective Function of ST2+ Treg Cells. J. Immunol. 196, 51.7-51.7 (2016).
21. Buonomo, E. L. et al. Role of interleukin 23 signaling in *Clostridium difficile* colitis. in Journal of Infectious Diseases 208, 917-920 (2013).
22. Buonomo, E. L. et al. Microbiota-Regulated IL-25 Increases Eosinophil Number to Provide Protection during *Clostridium difficile* Infection. Cell Rep. 1-12 (2016). doi:10.1016/j.celrep.2016.06.007
23. Kuehne, S. A. et al. Importance of toxin a, toxin b, and cdt in virulence of an epidemic *Clostridium Difficile* Strain. J. Infect. Dis. 209, 83-86 (2014).
24. Petri W A Jr., Buonomo E L. U.S. Provisional Patent Application Ser. No. 62/060,725 Filed on Oct. 7, 2014; U.S. patent application Ser. No. 15/517,191. Title: Compositions and Methods for Preventing and Treating Infection.
25. Cowardin C A, Petri W A Jr. U.S. Provisional Patent Application Ser. No. 62/339,283. Filed on May 20, 2016; U.S. patent application Ser. No. 15/597,384. Title: Compositions and Methods for Preventing and Treating *Clostridium Difficile* Infection.

What is claimed is:

1. A method for treating *Clostridium difficile* infection, said method comprising administering to a subject in need thereof a pharmaceutical composition comprising an effective amount of an Interleukin-33 protein, wherein the Interleukin-33 protein has an amino acid sequence that is at least 95% identical to SEQ ID NO: 8 or SEQ ID NO: 9.

2. The method of claim 1, wherein said Interleukin-33 protein has an amino acid sequence that is SEQ ID NO: 8 or SEQ ID NO: 9.

3. The method of claim 1, wherein said pharmaceutical composition comprises at least one additional therapeutic agent.

4. The method of claim 3, wherein said at least one additional therapeutic agent is selected from the group consisting of anesthetic, analgesic, antimicrobial, steroid, growth factor, cytokine, and anti-inflammatory agent.

5. The method of claim 4, wherein at least one of said additional therapeutic agents is an antimicrobial agent, wherein said antimicrobial agent is selected from the group consisting of antibacterial, antifungal, and antiviral agents.

6. The method of claim 5, wherein said at least one antibiotic is selected from the group consisting of vancomycin, fidaxomicin, metronidazole, nitazoxanide, and rifaximin.

7. The method of claim 1, wherein said Interleukin-33 is administered at a dosage ranging from about 0.1 µg/kg body weight to about 1,000 µg/kg body weight.

8. The method of claim 7, wherein said dosage is from about 1.0 µg/kg body weight to about 500 µg/kg body weight.

9. The method of claim 8, wherein said dosage is from about 5.0 µg/kg body weight to about 200 µg/kg body weight.

10. The method of claim 9, wherein said dosage is from about 10 µg/kg body weight to about 100 µg/kg body weight.

11. The method of claim 7, wherein said dosage is selected from the group consisting of 1.0, 5.0, 10, 15, 20, 25, 30, 50, 75, 100, 150 and 500 µg/kg of body weight.

12. The method of claim 1, wherein said pharmaceutical composition is administered at least twice.

13. The method of claim 12, wherein said pharmaceutical composition is administered up to 10 times.

14. The method of claim 1, wherein said method reduces mortality.

15. The method of claim 1, wherein said method prevents or inhibits recurrent infection.

16. The method of claim 1, wherein said method inhibits weight loss.

17. The method of claim 1, wherein said method inhibits diarrhea.

18. The method of claim 1, wherein said method inhibits colonic inflammation.

19. The method of claim 18, wherein said colonic inflammation is neutrophil inflammation.

20. The method of claim 18, wherein said colonic inflammation is monocyte inflammation.

21. The method of claim 1, wherein said method increases colonic Foxp3+ST2+ regulatory T cells during said infection.

22. The method of claim 1, wherein said pharmaceutical composition further comprises an effective amount of an inhibitor of Toll-Like Receptor 2 (TLR2), wherein said inhibitor inhibits stimulation of TLR2 activity by *Clostridium difficile* transferase toxin, thereby inhibiting the effects of *Clostridium difficile* transferase toxin.

23. A kit comprising a pharmaceutical composition of claim 1, optionally an additional therapeutic agent, an applicator, and an instructional material for the use thereof.

* * * * *

SEQUENCE LISTING

<160> NUMBER OF SEQ ID NOS: 12

<210> SEQ ID NO 1
<211> LENGTH: 270
<212> TYPE: PRT
<213> ORGANISM: Homo sapiens

<400> SEQUENCE: 1

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
```

```
                145                 150                 155                 160
Leu Ser Tyr Tyr Glu Ser Gln His Pro Ser Asn Glu Ser Gly Asp Gly
                    165                 170                 175

Val Asp Gly Lys Met Leu Met Val Thr Leu Ser Pro Thr Lys Asp Phe
                180                 185                 190

Trp Leu His Ala Asn Asn Lys Glu His Ser Val Glu Leu His Lys Cys
                195                 200                 205

Glu Lys Pro Leu Pro Asp Gln Ala Phe Phe Val Leu His Asn Met His
            210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
                260                 265                 270

<210> SEQ ID NO 2
<211> LENGTH: 264
<212> TYPE: PRT
<213> ORGANISM: Homo sapiens

<400> SEQUENCE: 2

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
            35                  40                  45

Ser Gly Leu Met Ile Lys Lys Glu Ala Cys Tyr Phe Arg Arg Glu Thr
        50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
                100                 105                 110

Ile Thr Glu Tyr Leu Ala Ser Leu Ser Thr Tyr Asn Asp Gln Ser Ile
            115                 120                 125

Thr Phe Ala Leu Glu Asp Glu Ser Tyr Glu Ile Tyr Val Glu Asp Leu
        130                 135                 140

Lys Lys Asp Glu Lys Lys Asp Lys Val Leu Leu Ser Tyr Tyr Glu Ser
145                 150                 155                 160

Gln His Pro Ser Asn Glu Ser Gly Asp Gly Val Asp Gly Lys Met Leu
                165                 170                 175

Met Val Thr Leu Ser Pro Thr Lys Asp Phe Trp Leu His Ala Asn Asn
                180                 185                 190

Lys Glu His Ser Val Glu Leu His Lys Cys Glu Lys Pro Leu Pro Asp
            195                 200                 205

Gln Ala Phe Phe Val Leu His Asn Met His Ser Asn Cys Val Ser Phe
        210                 215                 220

Glu Cys Lys Thr Asp Pro Gly Val Phe Ile Gly Val Lys Asp Asn His
225                 230                 235                 240

Leu Ala Leu Ile Lys Val Asp Ser Ser Glu Asn Leu Cys Thr Glu Asn
                245                 250                 255
```

```
Ile Leu Phe Lys Leu Ser Glu Thr
            260

<210> SEQ ID NO 3
<211> LENGTH: 229
<212> TYPE: PRT
<213> ORGANISM: Homo sapiens

<400> SEQUENCE: 3

Met Tyr Phe Met Lys Leu Arg Ser Gly Leu Met Ile Lys Lys Glu Ala
1               5                   10                  15

Cys Tyr Phe Arg Arg Glu Thr Thr Lys Arg Pro Ser Leu Lys Thr Gly
            20                  25                  30

Arg Lys His Lys Arg His Leu Val Leu Ala Ala Cys Gln Gln Gln Ser
        35                  40                  45

Thr Val Glu Cys Phe Ala Phe Gly Ile Ser Gly Val Gln Lys Tyr Thr
    50                  55                  60

Arg Ala Leu His Asp Ser Ser Ile Thr Gly Ile Ser Pro Ile Thr Glu
65                  70                  75                  80

Tyr Leu Ala Ser Leu Ser Thr Tyr Asn Asp Gln Ser Ile Thr Phe Ala
                85                  90                  95

Leu Glu Asp Glu Ser Tyr Glu Ile Tyr Val Glu Asp Leu Lys Lys Asp
            100                 105                 110

Glu Lys Lys Asp Lys Val Leu Leu Ser Tyr Tyr Glu Ser Gln His Pro
        115                 120                 125

Ser Asn Glu Ser Gly Asp Gly Val Asp Gly Lys Met Leu Met Val Thr
    130                 135                 140

Leu Ser Pro Thr Lys Asp Phe Trp Leu His Ala Asn Asn Lys Glu His
145                 150                 155                 160

Ser Val Glu Leu His Lys Cys Glu Lys Pro Leu Pro Asp Gln Ala Phe
                165                 170                 175

Phe Val Leu His Asn Met His Ser Asn Cys Val Ser Phe Glu Cys Lys
            180                 185                 190

Thr Asp Pro Gly Val Phe Ile Gly Val Lys Asp Asn His Leu Ala Leu
        195                 200                 205

Ile Lys Val Asp Ser Ser Glu Asn Leu Cys Thr Glu Asn Ile Leu Phe
    210                 215                 220

Lys Leu Ser Glu Thr
225

<210> SEQ ID NO 4
<211> LENGTH: 228
<212> TYPE: PRT
<213> ORGANISM: Homo sapiens

<400> SEQUENCE: 4

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Ile Ser Pro Ile Thr Glu Tyr
65                  70                  75                  80
```

-continued

```
Leu Ala Ser Leu Ser Thr Tyr Asn Asp Gln Ser Ile Thr Phe Ala Leu
                85                  90                  95
Glu Asp Glu Ser Tyr Glu Ile Tyr Val Glu Asp Leu Lys Lys Asp Glu
            100                 105                 110
Lys Lys Asp Lys Val Leu Leu Ser Tyr Tyr Glu Ser Gln His Pro Ser
        115                 120                 125
Asn Glu Ser Gly Asp Gly Val Asp Gly Lys Met Leu Met Val Thr Leu
    130                 135                 140
Ser Pro Thr Lys Asp Phe Trp Leu His Ala Asn Asn Lys Glu His Ser
145                 150                 155                 160
Val Glu Leu His Lys Cys Glu Lys Pro Leu Pro Asp Gln Ala Phe Phe
                165                 170                 175
Val Leu His Asn Met His Ser Asn Cys Val Ser Phe Glu Cys Lys Thr
            180                 185                 190
Asp Pro Gly Val Phe Ile Gly Val Lys Asp Asn His Leu Ala Leu Ile
        195                 200                 205
Lys Val Asp Ser Ser Glu Asn Leu Cys Thr Glu Asn Ile Leu Phe Lys
    210                 215                 220
Leu Ser Glu Thr
225

<210> SEQ ID NO 5
<211> LENGTH: 228
<212> TYPE: PRT
<213> ORGANISM: Homo sapiens

<400> SEQUENCE: 5

Met Lys Pro Lys Met Lys Tyr Ser Thr Asn Lys Ile Ser Thr Ala Lys
1               5                   10                  15
Trp Lys Asn Thr Ala Ser Lys Ala Leu Cys Phe Lys Leu Gly Lys Ser
            20                  25                  30
Gln Gln Lys Ala Lys Glu Val Cys Pro Met Tyr Phe Met Lys Leu Arg
        35                  40                  45
Ser Gly Leu Met Ile Lys Lys Glu Ala Cys Tyr Phe Arg Arg Glu Thr
    50                  55                  60
Thr Lys Arg Pro Ser Leu Lys Thr Gly Arg Lys His Lys Arg His Leu
65                  70                  75                  80
Val Leu Ala Ala Cys Gln Gln Gln Ser Thr Val Glu Cys Phe Ala Phe
                85                  90                  95
Gly Ile Ser Gly Val Gln Lys Tyr Thr Arg Ala Leu His Asp Ser Ser
            100                 105                 110
Ile Thr Asp Lys Val Leu Leu Ser Tyr Tyr Glu Ser Gln His Pro Ser
        115                 120                 125
Asn Glu Ser Gly Asp Gly Val Asp Gly Lys Met Leu Met Val Thr Leu
    130                 135                 140
Ser Pro Thr Lys Asp Phe Trp Leu His Ala Asn Asn Lys Glu His Ser
145                 150                 155                 160
Val Glu Leu His Lys Cys Glu Lys Pro Leu Pro Asp Gln Ala Phe Phe
                165                 170                 175
Val Leu His Asn Met His Ser Asn Cys Val Ser Phe Glu Cys Lys Thr
            180                 185                 190
Asp Pro Gly Val Phe Ile Gly Val Lys Asp Asn His Leu Ala Leu Ile
        195                 200                 205
Lys Val Asp Ser Ser Glu Asn Leu Cys Thr Glu Asn Ile Leu Phe Lys
    210                 215                 220
```

Leu Ser Glu Thr
225

<210> SEQ ID NO 6
<211> LENGTH: 222
<212> TYPE: PRT
<213> ORGANISM: Homo sapiens

<400> SEQUENCE: 6

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Ser Arg
            20                  25                  30

Lys His Lys Arg His Leu Val Leu Ala Ala Cys Gln Gln Gln Ser Thr
        35                  40                  45

Val Glu Cys Phe Ala Phe Gly Ile Ser Gly Val Gln Lys Tyr Thr Arg
    50                  55                  60

Ala Leu His Asp Ser Ser Ile Thr Glu Tyr Leu Ala Ser Leu Ser Thr
65                  70                  75                  80

Tyr Asn Asp Gln Ser Ile Thr Phe Ala Leu Glu Asp Glu Ser Tyr Glu
                85                  90                  95

Ile Tyr Val Glu Asp Leu Lys Lys Asp Glu Lys Lys Asp Lys Val Leu
            100                 105                 110

Leu Ser Tyr Tyr Glu Ser Gln His Pro Ser Asn Glu Ser Gly Asp Gly
        115                 120                 125

Val Asp Gly Lys Met Leu Met Val Thr Leu Ser Pro Thr Lys Asp Phe
    130                 135                 140

Trp Leu His Ala Asn Asn Lys Glu His Ser Val Glu Leu His Lys Cys
145                 150                 155                 160

Glu Lys Pro Leu Pro Asp Gln Ala Phe Phe Val Leu His Asn Met His
                165                 170                 175

Ser Asn Cys Val Ser Phe Glu Cys Lys Thr Asp Pro Gly Val Phe Ile
            180                 185                 190

Gly Val Lys Asp Asn His Leu Ala Leu Ile Lys Val Asp Ser Ser Glu
        195                 200                 205

Asn Leu Cys Thr Glu Asn Ile Leu Phe Lys Leu Ser Glu Thr
    210                 215                 220

<210> SEQ ID NO 7
<211> LENGTH: 180
<212> TYPE: PRT
<213> ORGANISM: Homo sapiens

<400> SEQUENCE: 7

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Tyr
            20                  25                  30

Leu Ala Ser Leu Ser Thr Tyr Asn Asp Gln Ser Ile Thr Phe Ala Leu
        35                  40                  45

Glu Asp Glu Ser Tyr Glu Ile Tyr Val Glu Asp Leu Lys Lys Asp Glu
    50                  55                  60

Lys Lys Asp Lys Val Leu Leu Ser Tyr Tyr Glu Ser Gln His Pro Ser
65                  70                  75                  80

Asn Glu Ser Gly Asp Gly Val Asp Gly Lys Met Leu Met Val Thr Leu
                85                  90                  95

Ser Pro Thr Lys Asp Phe Trp Leu His Ala Asn Asn Lys Glu His Ser
            100                 105                 110

Val Glu Leu His Lys Cys Glu Lys Pro Leu Pro Asp Gln Ala Phe Phe
        115                 120                 125

Val Leu His Asn Met His Ser Asn Cys Val Ser Phe Glu Cys Lys Thr
130                 135                 140

Asp Pro Gly Val Phe Ile Gly Val Lys Asp Asn His Leu Ala Leu Ile
145                 150                 155                 160

Lys Val Asp Ser Ser Glu Asn Leu Cys Thr Glu Asn Ile Leu Phe Lys
                165                 170                 175

Leu Ser Glu Thr
            180

<210> SEQ ID NO 8
<211> LENGTH: 160
<212> TYPE: PRT
<213> ORGANISM: Homo sapiens

<400> SEQUENCE: 8

Met Ser Ile Thr Gly Ile Ser Pro Ile Thr Glu Tyr Leu Ala Ser Leu
1               5                   10                  15

Ser Thr Tyr Asn Asp Gln Ser Ile Thr Phe Ala Leu Glu Asp Glu Ser
            20                  25                  30

Tyr Glu Ile Tyr Val Glu Asp Leu Lys Lys Asp Glu Lys Lys Asp Lys
        35                  40                  45

Val Leu Leu Ser Tyr Tyr Glu Ser Gln His Pro Ser Asn Glu Ser Gly
50                  55                  60

Asp Gly Val Asp Gly Lys Met Leu Met Val Thr Leu Ser Pro Thr Lys
65                  70                  75                  80

Asp Phe Trp Leu His Ala Asn Asn Lys Glu His Ser Val Glu Leu His
                85                  90                  95

Lys Cys Glu Lys Pro Leu Pro Asp Gln Ala Phe Phe Val Leu His Asn
            100                 105                 110

Met His Ser Asn Cys Val Ser Phe Glu Cys Lys Thr Asp Pro Gly Val
        115                 120                 125

Phe Ile Gly Val Lys Asp Asn His Leu Ala Leu Ile Lys Val Asp Ser
130                 135                 140

Ser Glu Asn Leu Cys Thr Glu Asn Ile Leu Phe Lys Leu Ser Glu Thr
145                 150                 155                 160

<210> SEQ ID NO 9
<211> LENGTH: 159
<212> TYPE: PRT
<213> ORGANISM: Homo sapiens

<400> SEQUENCE: 9

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
50                  55                  60

Gly Val Asp Gly Lys Met Leu Met Val Thr Leu Ser Pro Thr Lys Asp
65                  70                  75                  80

```
Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
            100                 105                 110

His Ser Asn Cys Val Ser Phe Glu Cys Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr
145                 150                 155

<210> SEQ ID NO 10
<211> LENGTH: 144
<212> TYPE: PRT
<213> ORGANISM: Homo sapiens

<400> SEQUENCE: 10

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Asn Lys
            20                  25                  30

Val Leu Leu Ser Tyr Tyr Glu Ser Gln His Pro Ser Asn Glu Ser Gly
        35                  40                  45

Asp Gly Val Asp Gly Lys Met Leu Met Val Thr Leu Ser Pro Thr Lys
    50                  55                  60

Asp Phe Trp Leu His Ala Asn Asn Lys Glu His Ser Val Glu Leu His
65                  70                  75                  80

Lys Cys Glu Lys Pro Leu Pro Asp Gln Ala Phe Phe Val Leu His Asn
                85                  90                  95

Met His Ser Asn Cys Val Ser Phe Glu Cys Lys Thr Asp Pro Gly Val
            100                 105                 110

Phe Ile Gly Val Lys Asp Asn His Leu Ala Leu Ile Lys Val Asp Ser
        115                 120                 125

Ser Glu Asn Leu Cys Thr Glu Asn Ile Leu Phe Lys Leu Ser Glu Thr
    130                 135                 140

<210> SEQ ID NO 11
<211> LENGTH: 266
<212> TYPE: PRT
<213> ORGANISM: Mus musculus

<400> SEQUENCE: 11

Met Arg Pro Arg Met Lys Tyr Ser Asn Ser Lys Ile Ser Pro Ala Lys
1               5                   10                  15

Phe Ser Ser Thr Ala Gly Glu Ala Leu Val Pro Pro Cys Lys Ile Arg
            20                  25                  30

Arg Ser Gln Gln Lys Thr Lys Glu Phe Cys His Val Tyr Cys Met Arg
        35                  40                  45

Leu Arg Ser Gly Leu Thr Ile Arg Lys Glu Thr Ser Tyr Phe Arg Lys
    50                  55                  60

Glu Pro Thr Lys Arg Tyr Ser Leu Lys Ser Gly Thr His Glu Glu
65                  70                  75                  80

Asn Phe Ser Ala Tyr Pro Arg Asp Ser Arg Lys Arg Ser Leu Leu Gly
                85                  90                  95

Ser Ile Gln Ala Phe Ala Ala Ser Val Asp Thr Leu Ser Ile Gln Gly
            100                 105                 110
```

```
Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
        130                 135                 140

Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Val Met Val Asn Met Ser Pro Ile Lys Asp Thr Asp Ile Trp
                180                 185                 190

Leu His Ala Asn Asp Lys Asp Tyr Ser Val Glu Leu Gln Arg Gly Asp
        195                 200                 205

Val Ser Pro Pro Glu Gln Ala Phe Phe Val Leu His Lys Lys Ser Ser
        210                 215                 220

Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
                245                 250                 255

Asn Asn Ile Met Phe Lys Leu Ser Lys Ile
                260                 265

<210> SEQ ID NO 12
<211> LENGTH: 158
<212> TYPE: PRT
<213> ORGANISM: Mus musculus

<400> SEQUENCE: 12

Ser Ile Gln Gly Thr Ser Leu Leu Thr Gln Ser Pro Ala Ser Leu Ser
1               5                   10                  15

Thr Tyr Asn Asp Gln Ser Val Ser Phe Val Leu Glu Asn Gly Cys Tyr
                20                  25                  30

Val Ile Asn Val Asp Asp Ser Gly Lys Asp Gln Glu Gln Asp Gln Val
            35                  40                  45

Leu Leu Arg Tyr Tyr Glu Ser Pro Cys Pro Ala Ser Gln Ser Gly Asp
        50                  55                  60

Gly Val Asp Gly Lys Lys Val Met Val Asn Met Ser Pro Ile Lys Asp
65                  70                  75                  80

Thr Asp Ile Trp Leu His Ala Asn Asp Lys Asp Tyr Ser Val Glu Leu
                85                  90                  95

Gln Arg Gly Asp Val Ser Pro Pro Glu Gln Ala Phe Phe Val Leu His
                100                 105                 110

Lys Lys Ser Ser Asp Phe Val Ser Phe Glu Cys Lys Asn Leu Pro Gly
            115                 120                 125

Thr Tyr Ile Gly Val Lys Asp Asn Gln Leu Ala Leu Val Glu Glu Lys
        130                 135                 140

Asp Glu Ser Cys Asn Asn Ile Met Phe Lys Leu Ser Lys Ile
145                 150                 155
```